United States Patent
Stahl et al.

(10) Patent No.: US 10,704,082 B2
(45) Date of Patent: *Jul. 7, 2020

(54) METHODS OF NUCLEIC ACID SAMPLE PREPARATION

(71) Applicant: ArcherDX, Inc., Boulder, CO (US)

(72) Inventors: Joshua Stahl, Boulder, CO (US); Jason Myers, Boulder, CO (US); Brady Culver, Beverly, MA (US); Brian Kudlow, Boulder, CO (US)

(73) Assignee: ArcherDX, Inc., Boulder, CO (US)

( * ) Notice: Subject to any disclaimer, the term of this patent is extended or adjusted under 35 U.S.C. 154(b) by 119 days.

This patent is subject to a terminal disclaimer.

(21) Appl. No.: 15/706,642

(22) Filed: Sep. 15, 2017

(65) Prior Publication Data

US 2018/0127806 A1 May 10, 2018

Related U.S. Application Data

(60) Provisional application No. 62/395,339, filed on Sep. 15, 2016.

(51) Int. Cl.
| | |
|---|---|
| *C12Q 1/6806* | (2018.01) |
| *C12N 15/10* | (2006.01) |
| *C12Q 1/6853* | (2018.01) |
| *C12Q 1/6855* | (2018.01) |

(52) U.S. Cl.
CPC ....... *C12Q 1/6806* (2013.01); *C12N 15/1096* (2013.01); *C12Q 1/6853* (2013.01); *C12Q 1/6855* (2013.01)

(58) Field of Classification Search
None
See application file for complete search history.

(56) References Cited

U.S. PATENT DOCUMENTS

| | | | |
|---|---|---|---|
| 5,374,524 A | 12/1994 | Miller | |
| 5,827,658 A | 10/1998 | Liang | |
| 6,818,395 B1 | 11/2004 | Quake et al. | |
| 6,911,345 B2 | 6/2005 | Quake et al. | |
| 7,169,560 B2 | 1/2007 | Lapidus et al. | |
| 7,220,549 B2 | 5/2007 | Buzby | |
| 7,226,720 B2 | 6/2007 | Wisnudel et al. | |
| 7,279,563 B2 | 10/2007 | Kwiatkowski | |
| 7,282,337 B1 | 10/2007 | Harris | |
| 8,067,434 B2 | 11/2011 | Ibrahim et al. | |
| 2006/0252077 A1 | 11/2006 | Buzby | |
| 2007/0070349 A1 | 3/2007 | Harris et al. | |
| 2009/0093378 A1 | 4/2009 | Bignell et al. | |
| 2011/0201507 A1 | 8/2011 | Rava et al. | |
| 2011/0201598 A1 | 8/2011 | Gujral et al. | |
| 2013/0303461 A1* | 11/2013 | Iafrate .................. | C12Q 1/6874 514/19.3 |
| 2015/0211050 A1 | 7/2015 | Iafrate et al. | |
| 2015/0252361 A1 | 9/2015 | Hayden et al. | |
| 2018/0127807 A1 | 5/2018 | Stahl et al. | |

FOREIGN PATENT DOCUMENTS

| | | |
|---|---|---|
| WO | WO 2001/083696 A2 | 11/2001 |
| WO | WO 2004/079326 A2 | 9/2004 |
| WO | WO 2006/034833 A1 | 4/2006 |

OTHER PUBLICATIONS

Bowman et al. BMC Genomics 2013; 14: 466 (Year: 2013).*
International Preliminary Report on Patentability for Application No. PCT/US2017/051924, dated Mar. 28, 2019.
International Search Report and Written Opinion for Application No. PCT/US2017/051924, dated Dec. 11, 2017.
International Preliminary Report on Patentability for Application No. PCT/US2017/051927, dated Mar. 28, 2019.
International Search Report and Written Opinion for Application No. PCT/US2017/051927, dated Dec. 1, 2017.
Akeno-Stuart et al., The RET kinase inhibitor NVP-AST487 blocks growth and calcitonin gene expression through distinct mechanisms in medullary thyroid cancer cells. Cancer Res. Jul. 15, 2007;67(14):6956-64.
Bentley, Whole-genome re-sequencing. Curr Opin Genet Dev. Dec. 2006;16(6):545-52. Epub Oct. 18, 2006.
Carlomagno et al., BAY 43/9006 inhibition of oncogenic RET mutants. J Natl Cancer Inst. Mar. 1, 2006;98(5):326-34.
Cuccuru et al., Cellular effects and antitumor activity of RET inhibitor RPI-1 on MEN2A-associated medullary thyroid carcinoma. J Natl Cancer Inst. Jul. 7, 2004;96(13):1006-14.
Das et al., Full-length cDNAs: more than just reaching the ends. Physiol Genomics. Jul. 17, 2001;6(2):57-80.
Freier et al., Improved free-energy parameters for predictions of RNA duplex stability. Proc Natl Acad Sci U S A. Dec. 1986; 83(24): 9373-9377. doi: 10.1073/pnas.83.24.9373.
Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006. Erratum in: Proc Natl Acad Sci U S A. Feb. 6, 2007;104(6):2025.
Grazma et al., Activity of novel RET inhibitors against RET genotypes associated with medullary thyroid cancer. J Clin Oncol. 2010;28:15s:5559. Epub Sep. 22, 2016. doi: 10/1200/jco.1010.28. 15_suppl.5559.
Hallberg et al., ALK and NSCLC: Targeted therapy with ALK Inhibitors. F1000 Med Reports 2011;3:21. Epub Nov. 1, 2011. doi: 10.3410/M3-21. 9 pages.
Kohno et al., KIF5B-RET fusions in lung adenocarcinoma. Nat Med. Feb. 12, 2012;18(3):375-7. doi: 10.1038/nm.2644.
Mardis, The impact of next-generation sequencing technology on genetics. Trends Genet. Mar. 2008;24(3):133-41. doi: 10.1016/j.tig. 2007.12.007. Epub Feb. 11, 2008.
Mologni et al., Inhibition of RET tyrosine kinase by SU5416. J Mol Endocrinol. Oct. 2006;37(2):199-212.

(Continued)

*Primary Examiner* — Angela M. Bertagna
(74) *Attorney, Agent, or Firm* — Wolf, Greenfield & Sacks, P.C.

(57) ABSTRACT

Aspects of the technology disclosed herein relate to methods of preparing and analyzing nucleic acids. In some embodiments, methods for preparing nucleic acids for sequence analysis (e.g., using next-generation sequencing) are provided herein.

27 Claims, 8 Drawing Sheets

Specification includes a Sequence Listing.

(56) References Cited

OTHER PUBLICATIONS

Mussolin et al., Plasma Cell-Free DNA in Paediatric Lymphomas. J Cancer. 2013; 4(4): 323-329. EPub Apr. 16, 2013. doi: 10.7150/jca.6226.

Nyrén et al., Solid phase DNA minisequencing by an enzymatic luminometric inorganic pyrophosphate detection assay. Anal Biochem. Jan. 1993;208(1):171-5.

Rikova et al., Global survey of phosphotyrosine signaling identifies oncogenic kinases in lung cancer. Cell. Dec. 14, 2007;131(6):1190-203.

Rumsby, An introduction to PCR techniques. Methods Mol Biol. 2006;324:75-89.

Sakamoto et al., CH5424802, a selective ALK inhibitor capable of blocking the resistant gatekeeper mutant. Cancer Cell. May 17, 2011;19(5):679-90. doi: 10.1016/j.ccr.2011.04.004.

Samadi et al., A novel RET inhibitor with potent efficacy against medullary thyroid cancer in vivo. Surgery. Dec. 2010;148(6):1228-36; discussion 1236. doi: 10.1016/j.surg.2010.09.026.

Shendure et al., Next-generation DNA sequencing. Nat Biotechnol. Oct. 2008;26(10):1135-45. doi: 10.1038/nbt1486.

Soda et al., Identification of the transforming EML4-ALK fusion gene in non-small-cell lung cancer. Nature. Aug. 2, 2007;448(7153):561-6. Epub Jul. 11, 2007.

Strausberg et al., Emerging DNA sequencing technologies for human genomic medicine. Drug Discov Today. Jul. 2008;13(13-14):569-77. doi: 10.1016/j.drudis.2008.03.025. Epub May 22, 2008.

Su et al., Next-generation sequencing and its applications in molecular diagnostics. Expert Rev Mol Diagn. Apr. 2011;11(3):333-43. doi: 10.1586/erm.11.3.

Ying, Complementary DNA libraries: an overview. Mol Biotechnol. Jul. 2004;27(3):245-52.

Zhang et al., The impact of next-generation sequencing on genomics. J Genet Genomics. Mar. 20, 2011;38(3):95-109. doi: 10.1016/j.jgg.2011.02.003. Epub Mar. 15, 2011. Author Manuscript.

Zou et al., An orally available small-molecule inhibitor of c-Met, PF-2341066, exhibits cytoreductive antitumor efficacy through antiproliferative and antiangiogenic mechanisms. Cancer Res. May 1, 2007;67(9):4408-17.

Mologni, Development of RET kinase inhibitors for targeted cancer therapy. Curr Med Chem. 2011;18(2):162-75.

* cited by examiner

METHODS OF NUCLEIC ACID SAMPLE PREPARATION

RELATED APPLICATIONS

This application claims priority under 35 U.S.C. § 119(e) to U.S. Provisional Patent Application No. 62/395,339, filed Sep. 15, 2016, which is hereby incorporated by reference in its entirety.

TECHNICAL FIELD

The technology described herein relates to methods and compositions useful in the preparation of nucleic acid molecules for analysis.

BACKGROUND

Target enrichment prior to next-generation sequencing is more cost-effective than whole genome, whole exome, and whole transcriptome sequencing and therefore more practical for broad implementation; both for research discovery and clinical applications. For example, high coverage depth afforded by target enrichment approaches enables a wider dynamic range for allele counting (in gene expression and copy number assessment) and detection of low frequency mutations, which is advantageous for evaluating somatic mutations in cancer. Examples of current enrichment protocols for next generation sequencing include hybridization-based capture assays (TruSeq Capture, Illumina; SureSelect Hybrid Capture, Agilent) and polymerase chain reaction (PCR)-based assays (HaloPlex, Agilent; AmpliSeq, Ion Torrent; TruSeq Amplicon, Illumina; emulsion/digital PCR, Raindance). Hybridization-based approaches capture not only the targeted sequences covered by the capture probes but also near off-target bases that consume sequencing capacity. In addition, these methods are relatively time-consuming, labor-intensive, and suffer from a relatively low level of specificity.

SUMMARY

Aspects of the technology disclosed herein relate to methods of preparing and analyzing nucleic acids. In some embodiments, methods and compositions useful in the preparation of nucleic acid samples for sequence analysis (e.g., using next-generating sequencing) are provided herein. In some embodiments, techniques described herein are related to methods of determining a nucleic acid sequence. In some embodiments, methods and compositions described herein relate to the enrichment of nucleic acids comprising one or more target nucleotide sequences prior to sequencing. In some aspects, the disclosure provides methods of preparing nucleic acids (e.g., for use in a sequencing analysis) that involve adding one or more capture moiety modified nucleotides to a nucleic acid. In some embodiments, the methods further involve ligating an adapter nucleic acid to the nucleic acid to which the capture moiety modified nucleotide has been added to produce a ligation product. In some embodiments, the methods further involve capturing the ligation product by contacting the ligation product with a binding partner of a capture moiety of the capture moiety modified nucleotide. In some embodiments, the methods further involve amplifying the ligation product, e.g., by polymerase chain reaction or another suitable amplification approach. In some embodiments, methods are provided for preparing nucleic acids that involve adding one or more nucleotides to a 3' end of a nucleic acid (e.g., a double-stranded nucleic acid) comprising a target nucleotide sequence, in which at least one of the one or more nucleotides is a capture moiety modified nucleotide. In some embodiments, presence of the capture moiety modified nucleotide at the 3'-end of the nucleic acid facilitates isolation, purification and/or washing of the nucleic acid while avoiding incorporation of modified nucleotides (e.g., randomly) throughout the nucleic acid. In some embodiments, methods are provided for preparing nucleic acids that involve incorporating one or more nucleotides into a nucleic acid (e.g., a double-stranded nucleic acid) comprising a target nucleotide sequence, in which at least one of the one or more nucleotides is a capture moiety modified nucleotide. In some embodiments, the one or more nucleotides are incorporated using a primer (e.g., a reverse transcription primer). In some embodiments, the one or more nucleotides are incorporated during an earlier step of preparing the nucleic acids. For example, in some embodiments, the one or more nucleotides are incorporated during fragmentation, random priming, first strand synthesis, second strand synthesis, and/or end repair.

In some aspects, the disclosure provides methods of preparing nucleic acids for analysis, in which the methods involve: (a) adding one or more nucleotides to a 3' end of a double-stranded nucleic acid comprising a target nucleotide sequence, wherein at least one of the one or more nucleotides is a capture moiety modified nucleotide; (b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double-stranded nucleic acid in step (a); (c) capturing the ligation product by contacting the ligation product with a binding partner of a capture moiety of the capture moiety modified nucleotide; and (d) amplifying the ligation product by polymerase chain reaction using a first target-specific primer that specifically anneals to the target nucleotide sequence and a first adapter primer that specifically anneals to a complementary sequence of the adapter nucleic acid.

In some embodiments, step (b) comprises combining the adapter nucleic acid, the double-stranded nucleic acid, and a ligase under conditions in which the ligase ligates the adapter nucleic acid to the double-stranded nucleic acid. In some embodiments, the adapter nucleic acid that is combined with the double-stranded nucleic acid comprises a duplex portion and an overhang sequence. In some embodiments, the overhang sequence comprises the sequence of one or more nucleotides at the 3' end of the adapter nucleic acid that is complementary with the one or more nucleotides added to the 3' end of the double stranded nucleic acid in step (a).

In some embodiments, step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

In some embodiments, methods provided herein further comprise: (e) amplifying an amplification product of step (d) by polymerase chain reaction using a second adapter primer and a second target-specific primer. In some embodiments, the second target-specific primer is nested relative to the first target-specific primer. In some embodiments, the second target-specific primer comprises a 5' tail that does not anneal to the target nucleotide sequence. In some embodiments, the method further comprises adding an additional primer comprising a 3' portion that is identical to the 5' tail of the second target-specific primer.

In some embodiments, the capture moiety is a biotin moiety. In some embodiments, the biotin moiety comprises biotin-triethylene glycol, bis-biotin, photocleavable biotin, desthiobiotin, desthiobiotin-triethylene glycol, or biotin azide.

In some embodiments, the capture moiety modified nucleotide comprises a nucleobase selected from the group consisting of adenine, guanine, thymine, uracil, and cytosine, or a derivative thereof. In some embodiments, the capture moiety modified nucleotide comprises an adenine nucleobase or derivative thereof. In some embodiments, the capture moiety is covalently linked to the adenine nucleobase or derivative thereof at position 5, 6, 7 or 8. In some embodiments, the capture moiety is covalently linked to the adenine nucleobase at position 7. In some embodiments, position 7 of the adenine nucleobase is a carbon atom.

In some embodiments, the biotin moiety is covalently linked to the nucleobase via a linker of any appropriate length. In some embodiments, the biotin moiety is covalently linked to the nucleobase, e.g., via a linker of 5 to 20 atoms in length (e.g., 5, 6, 7, 8, 9, 10, 11, 12, 13, 14, 15, 16, 17, 18, 19, 20 atoms in length). In some embodiments, the capture moiety modified nucleotide is biotin-n-dNTP, wherein n is an integer from 5 to 20 representing the number of linker atoms between a carbonyl-group of the biotin moiety and the position of attachment on a nucleobase of the NTP.

In some embodiments, the binding partner is streptavidin. In some embodiments, the streptavidin is attached to a paramagnetic bead.

In some embodiments, in step (a), one nucleotide is added to the 3' end of the double-stranded nucleic acid comprising the target nucleotide sequence.

In some embodiments, methods further comprise a purification of non-specific nucleic acids. In some embodiments, methods provided herein further comprise a reaction cleanup or a washing step after step (b) and before step (c). In some embodiments, the method further comprises, after step (c) and prior to step (d): i) immobilizing the double-stranded nucleic acid, which comprises the capture moiety modified nucleotide, on a paramagnetic substrate or surface (e.g., a polystyrene paramagnetic bead); and ii) washing the immobilized double-stranded nucleic acid. In some embodiments, the method further comprises, after step (ii): iii) releasing the washed immobilized double-stranded nucleic acid from the paramagnetic substrate or surface. In some embodiments, the washed immobilized double-stranded nucleic acid is released from the paramagnetic substrate or surface by contacting with a chemical reagent and/or applying heat. In some embodiments, the chemical reagent is a base or basic solution. In some embodiments, the chemical reagent comprises sodium hydroxide (NaOH). It should be appreciated that, in some embodiments, contacting can involve mixing two solutions (e.g., a solution comprising a base and a soluton comprising a washed immobilized nucleic acid), adding a solid to a solution, or adding a solution to a solid. In some embodiments, the washed immobilized double-stranded nucleic acid is released from the paramagnetic substrate or surface by contacting with NaOH and heating (e.g., heating to above room temperature, such as a temperature in a range of 25 to 90° C., 25 to 70° C., 25 to 50° C., 35 to 65° C., 35 to 45° C., 30 to 40° C., 40 to 50° C.). In some embodiments, the washed immobilized double-stranded nucleic acid remains on the paramagnetic substrate or surface, e.g., for further preparation for analysis. In some embodiments, the washed immobilized double-stranded nucleic acid is released from the paramagnetic substrate or surface prior to further preparation for analysis.

In some embodiments, methods provided herein further comprise, prior to step (a), 5' phosphorylating the double-stranded nucleic acid.

In some embodiments, method provided herein further comprise, prior to step (a): i) preparing cDNA by conducting a randomly-primed first strand synthesis reaction using an RNA preparation as a template and a second strand synthesis reaction using a product of the randomly-primed first strand synthesis reaction as a template; and ii) end repairing the cDNA to produce a blunt-ended, double-stranded nucleic acid. In some embodiments, the method further comprises, after step ii): iii) immobilizing the double-stranded nucleic acid, which comprises the capture moiety modified nucleotide, on a paramagnetic substrate or surface; iv) washing the immobilized double-stranded nucleic acid; and v) releasing the washed immobilized double-stranded nucleic acid from the paramagnetic substrate or surface. In some embodiments, the paramagnetic substrate or surface comprises a coating (e.g., a polystyrene coating). In some embodiments, cDNA is prepared for analysis by conducting gene specifically-primed first strand synthesis. In some embodiments, end repairing involves blunting and/or phosphorylating DNA ends.

In some embodiments, methods further comprise, after step (e), (f) immobilizing the amplification product of step (e) on a paramagnetic substrate or surface; (g) washing the immobilized amplification product; and (h) releasing the washed immobilized amplification product from the paramagnetic substrate or surface. In some embodiments, the method further comprises one or more intervening washing steps (e.g., washing of amplification products between any step of the methods described herein). For example, in some embodiments, the method further comprises a washing step after step (e) and before step (f).

In some embodiments, in step (b), the double-stranded nucleic acid is ligated to the adapter nucleic acid in the presence of a crowding agent. In some embodiments, the crowding agent is polyethylene glycol in an amount representing 5% to 50% of a ligation mixture. In some embodiments, the double-stranded nucleic acid is blunt-ended. In some embodiments, the double-stranded nucleic acid comprises overhangs.

In some aspects, the disclosure provides methods of preparing nucleic acids for analysis, in which the methods involve: (a) preparing a cDNA by conducting a randomly-primed first strand synthesis reaction using an RNA preparation as a template and a second strand synthesis reaction using a product of the randomly-primed first strand synthesis reaction as a template, wherein the RNA preparation comprises a target nucleotide sequence; (b) end repairing the cDNA to produce a blunt-ended, double-stranded nucleic acid comprising the target nucleotide sequence; (c) immobilizing the blunt-ended, double-stranded nucleic acid on a paramagnetic substrate or surface; (d) washing the immobilized blunt-ended, double-stranded nucleic acid; (e) releasing the washed immobilized blunt-ended, double-stranded nucleic acid from the paramagnetic substrate or surface; (f) adding one or more nucleotides to the 3' end of the released blunt-ended, double-stranded nucleic acid; (g) ligating an adapter that comprises a ligatable duplex portion and an overhang sequence to the nucleic acid produced in step (f) to produce a ligation product, wherein the overhang sequence is complementary with the one or more nucleotides; (h) amplifying the ligation product by polymerase chain reaction using a first target-specific primer that specifically anneals to the target nucleotide sequence and a first adapter primer that specifically anneals to a complementary sequence of the adapter nucleic acid; (i) amplifying an amplification product of step (h) by polymerase chain reaction using a second adapter primer and a second target-specific primer, wherein the second target-specific primer is nested relative to the first target-specific primer; (j) immobilizing the amplification product of step (i) to a paramagnetic substrate or surface; (k) washing the immobilized amplification product; and (l) releasing the washed immobilized amplification product from the paramagnetic substrate or surface. In some embodiments, step (h) is performed without washing the ligation product.

In some aspects, the disclosure provides methods of preparing nucleic acids for analysis, in which the methods involve: (a) preparing a cDNA by conducting a randomly-primed first strand synthesis reaction using a nucleic acid preparation as a template and a second strand synthesis reaction using a product of the randomly-primed first strand synthesis reaction as a template, wherein the nucleic acid preparation comprises a target nucleotide sequence; (b) end repairing the cDNA to produce a blunt-ended, double-stranded nucleic acid comprising the target nucleotide sequence; (c) washing the blunt-ended, double-stranded nucleic acid; (d) adding one or more nucleotides to the 3' end of the nucleic acid washed in step (c), optionally wherein at least one of the one or more nucleotides is a capture moiety modified nucleotide; (e) washing the nucleic acid produced in step (d); (f) ligating an adapter nucleic acid that comprises a ligatable duplex portion and an overhang sequence to the nucleic acid washed in step (e) to produce a ligation product, wherein the overhang sequence is complementary with the one or more nucleotides; (g) amplifying the ligation product by polymerase chain reaction using a first target-specific primer that specifically anneals to the target nucleotide sequence and a first adapter primer that specifically anneals to a complementary sequence of the adapter nucleic acid; (h) amplifying an amplification product of step (g) by polymerase chain reaction using a second adapter primer and a second target-specific primer, wherein the second target-specific primer is nested relative to the first target-specific primer; and (j) washing the amplification product of step (h).

In some embodiments, the washing steps are performed using a solid-phase reversible immobilization technique.

In some embodiments, at least one of the one or more nucleotides is a capture moiety modified nucleotide, and the method further comprises, following step (f) and before step (g), capturing the ligation product using an immobilized binding partner of the capture moiety of the capture moiety modified nucleotide; and cleaning the captured ligation product. In some embodiments, the capture moiety comprises a biotin moiety and the binding partner comprises streptavidin.

In some embodiments, the second adapter primer is nested relative to the first adapter primer. In some embodiments, the second adapter primer specifically anneals to a complementary sequence of the adapter nucleic acid.

Other advantages and novel features of the present disclosure will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Among other aspects, the present disclosure provides improved techniques related to the preparation of nucleic acid sample libraries for analysis. As described herein, an adapter nucleic acid may be ligated to a nucleic acid comprising a target nucleotide sequence. The use of adapter nucleic acids can be useful during library preparation and sequencing analysis, for example, by providing primer binding sites and molecular barcode or index sequences. In some aspects, the present disclosure relates to improvements in processes related to adapter ligation and adapter-ligated sample isolation that substantially improves molecular barcode fidelity.

In some aspects, the disclosure relates to the recognition that, following adapter ligation, carryover of unligated adapter into subsequent PCR reactions could result in an overabundance of molecular barcodes. This overabundance, or inflation, of molecular barcodes can result in false positives, as one molecule should only contain one barcode. It is appreciated that, in some embodiments, unligated adapter can, in some instances, prime off of a common region in existing fragments during PCR. Over multiple reaction cycles, additional copies of a barcode or other artificial sequence can be integrated into a single molecule. Accordingly, the inventors have recognized and appreciated the need for improved processes relating to the ligation of adapters and the isolation of adapter-ligated library fragments.

In some aspects, the disclosure provides a method of preparing nucleic acids for analysis, comprising (a) adding a capture moiety modified nucleotide to a 3' end of a double-stranded nucleic acid (e.g., cDNA, gDNA), ligating an adapter nucleic acid to the double-stranded nucleic acid having the capture moiety modified nucleotide, and capturing the adapter-ligated nucleic acid with a binding partner of the capture moiety modified nucleotide.

Figure 1:
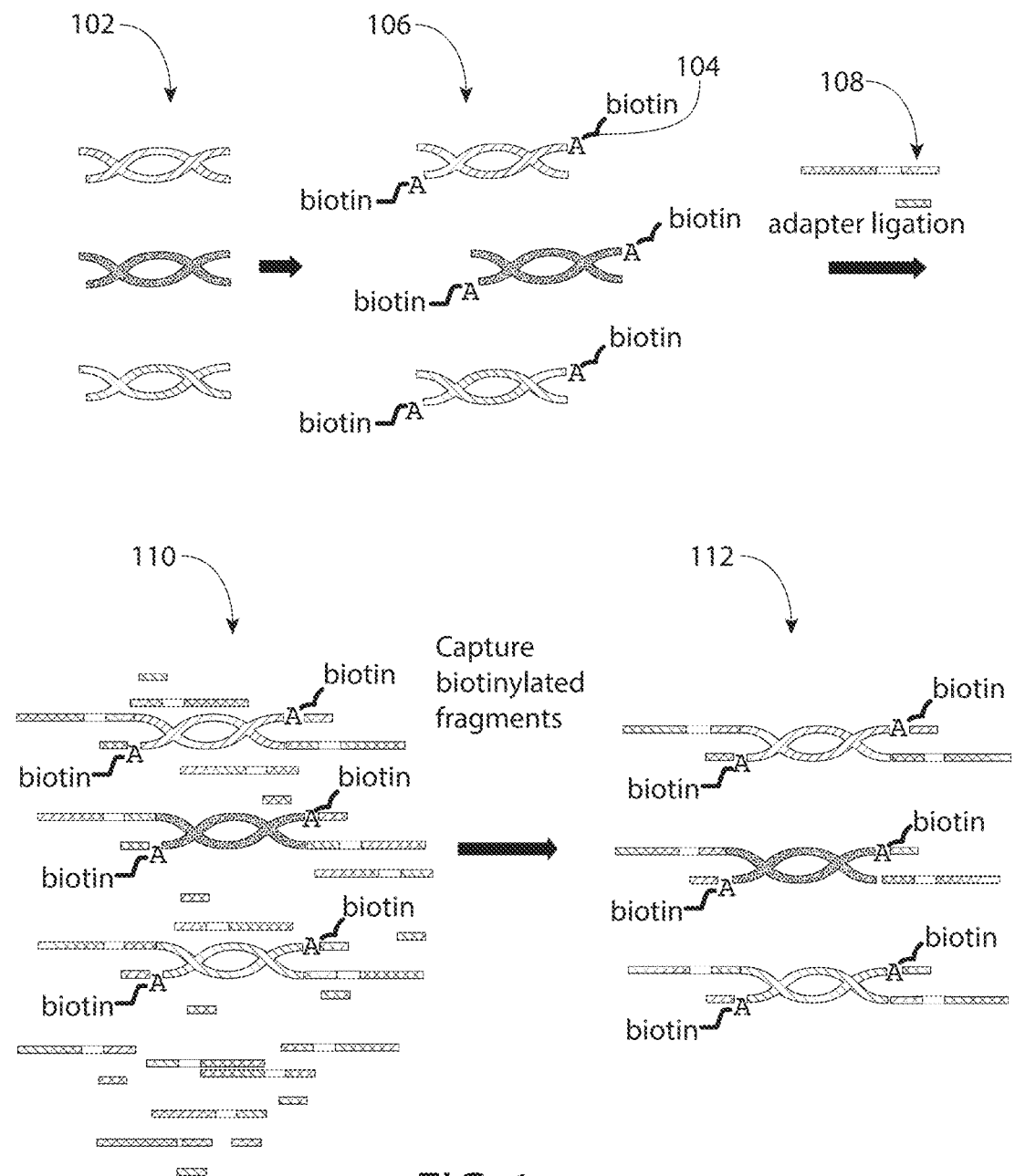
FIG. 1 is an illustration of a process that allows for the capture of an adapter-ligated nucleic acid library.

In some embodiments, the capture moiety modified nucleotide is a biotin moiety modified nucleotide. A general depiction of this method is shown in FIG. 1, which provides a non-limiting example of a method involving a biotin moiety modified nucleotide. In this embodiment, a library of blunt-ended, 5' phosphorylated double-stranded nucleic acids 102 is provided. Biotin-labeled ATP 104 is added to the 3' ends of the double-stranded nucleic acids to produce a library 106 comprising capture moiety modified nucleotides at the 3' ends of the fragments. The library fragments are ligated with an adapter 108 to produce a sample 110 having unligated adapter along with adapter-ligated library fragments. Ligated library fragments are captured, or isolated, from unligated adapter using a streptavidin coated surface to generate a library 112 that minimizes or eliminates the occurrence of unligated adapter carryover. Although this example utilizes a biotin capture moiety, any moiety that is capable of being specifically targeted for isolation (e.g., via an interaction with a binding partner) may be suitable in the techniques described herein.

Capture Moiety

Aspects of the techniques described herein relate to the use of a capture moiety to isolate a molecule of interest (e.g., a nucleic acid, a ligation product, etc.). As used herein, a "capture moiety" refers to a moiety that is configured to selectively interact with a binding partner for the purpose of capturing (e.g., isolating/purifying) the molecule of interest.

A capture moiety and a binding partner of the capture moiety may comprise any suitable binding pair. In some embodiments, a binding pair can selectively interact through covalent or non-covalent binding. In some embodiments, a binding pair can selectively interact by hybridization, ionic bonding, hydrogen bonding, van der Waals interactions, or any combination of these forces. In some embodiments, a capture moiety and/or binding partner can comprise, for example, biotin, avidin, streptavidin, digoxigenin, inosine, avidin, GST sequences, modified GST sequences, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

In some embodiments, a capture moiety comprises a biotin moiety. In some embodiments, techniques described herein are useful in preparing nucleic acid samples for analysis. Accordingly, in some embodiments, a nucleic acid molecule comprises a biotinylated capture moiety. In some embodiments, the nucleic acid molecule comprises at least one capture moiety modified nucleotide comprising a biotin moiety. In some embodiments, the capture moiety modified nucleotide comprises the general structure of formula (I):

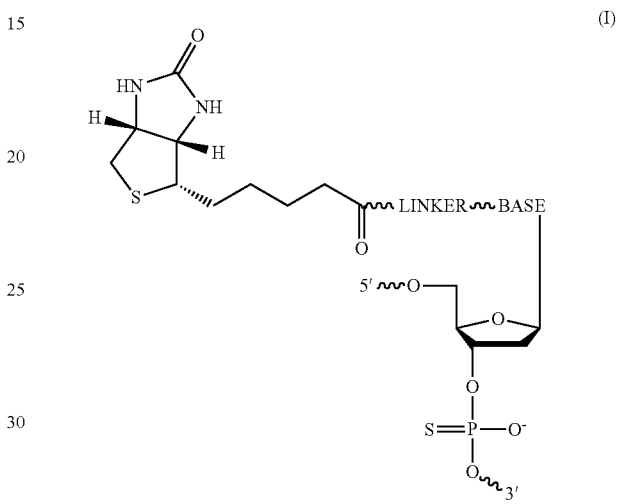

As shown in formula (I), a capture moiety modified nucleotide may comprise a biotin moiety attached to a nucleobase of a nucleotide. For example, in some embodiments, the biotin moiety comprises biotin-triethylene glycol, bis-biotin, photocleavable biotin, desthiobiotin, desthiobiotin-triethylene glycol, or biotin azide. Non-limiting examples of capture moiety modified nucleotides are shown in Table 1.

TABLE 1

Example structures of capture moiety modified nucleotides

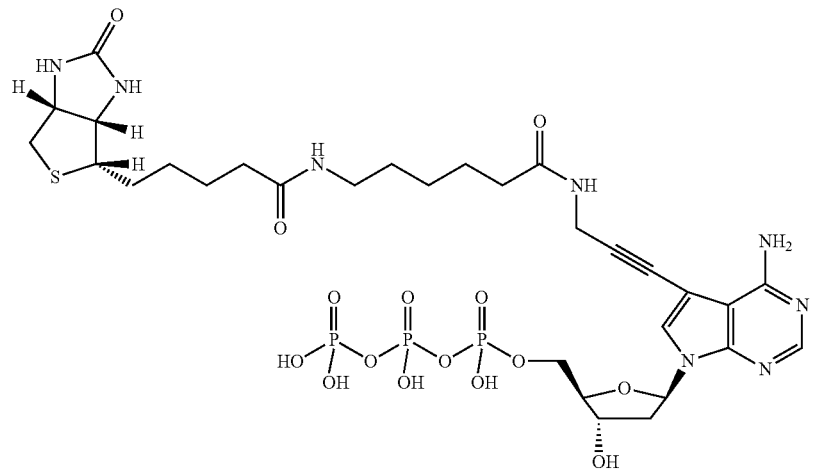 [SMILES: Nc1ncnc2c1c(C#CCNC(=O)CCCCCNC(=O)CCCC[C@@H]1SC[C@@H]3NC(=O)N[C@@H]31)cn2[C@H]1C[C@H](O)[C@@H](COP(=O)(O)OP(=O)(O)OP(=O)(O)O)O1]

Biotin-11-dATP

TABLE 1-continued
Example structures of capture moiety modified nucleotides
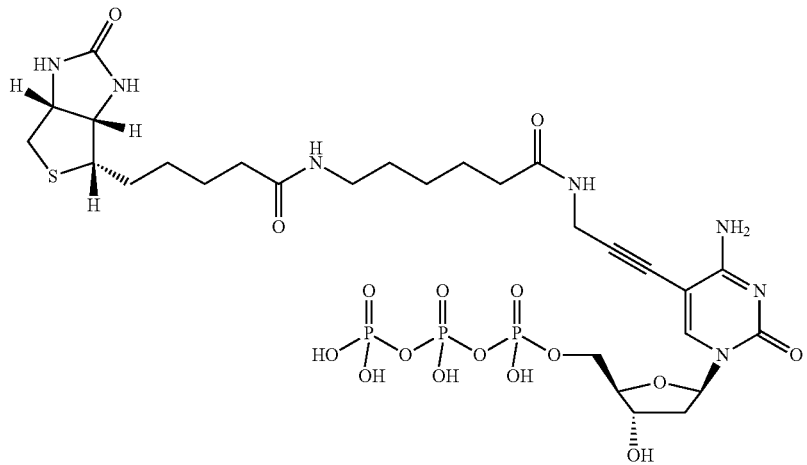 [SMILES: Nc1nc(=O)n([C@H]2C[C@H](O)[C@@H](COP(=O)(O)OP(=O)(O)OP(=O)(O)O)O2)cc1C#CCNC(=O)CCCCCNC(=O)CCCC[C@@H]1SC[C@@H]2NC(=O)N[C@@H]21]
Biotin-11-dCTP
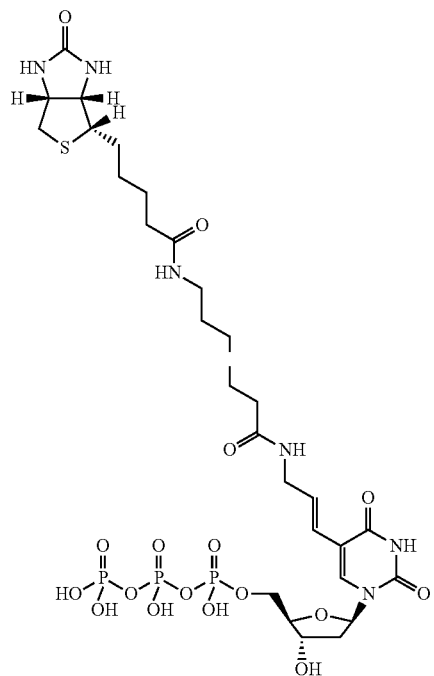
Biotin-11-dUTP

TABLE 1-continued
Example structures of capture moiety modified nucleotides
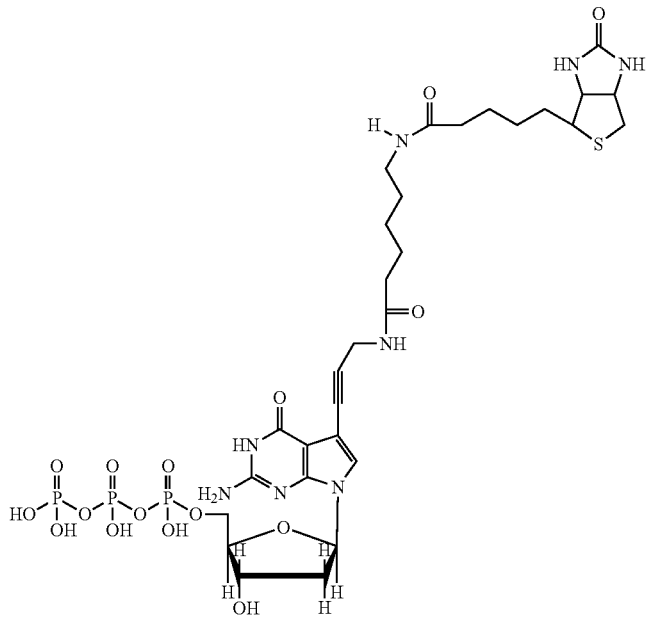
$C_{30}H_{45}N_8O_{16}P_3S$
898
Biotin-11-dGTP
| Thymidine | Spacer | Biotin |
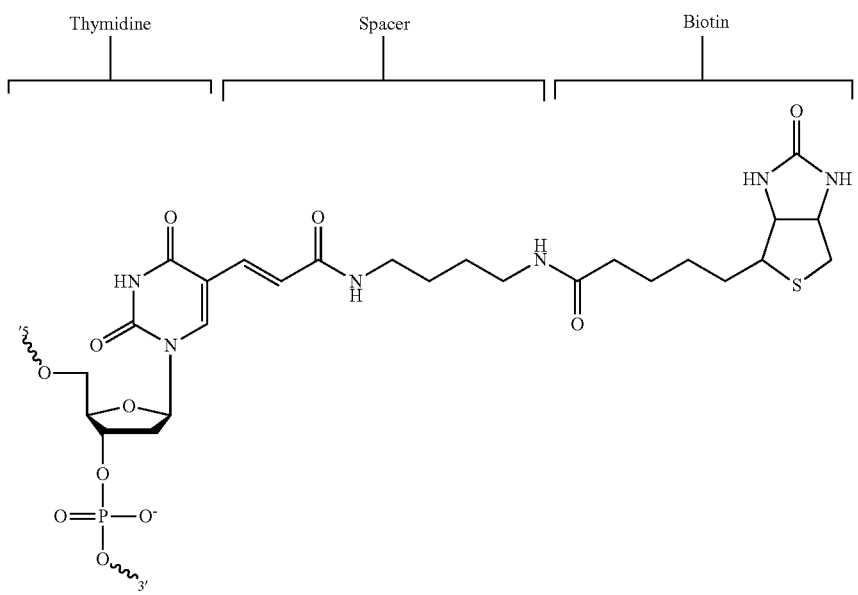

TABLE 1-continued

Example structures of capture moiety modified nucleotides

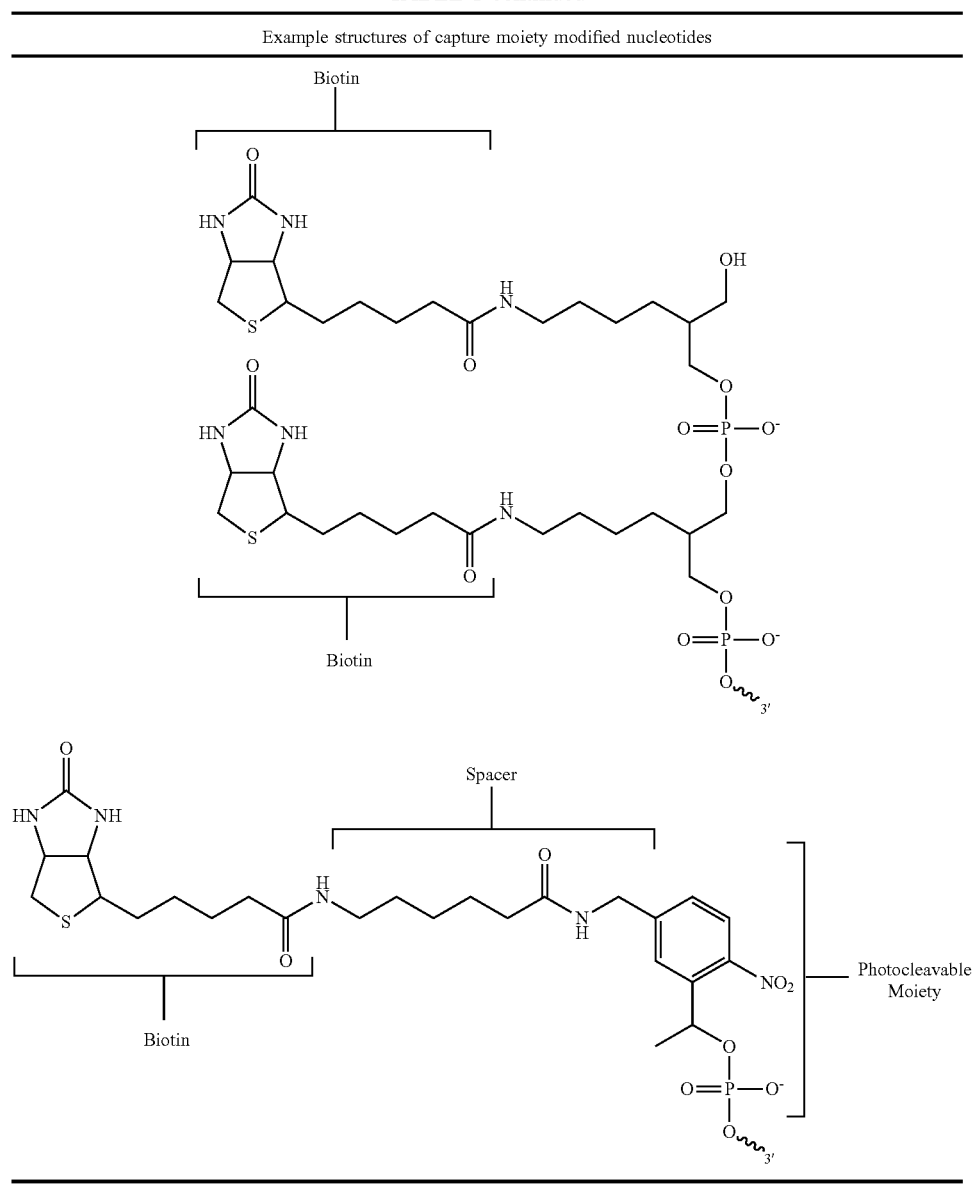

In some embodiments, a capture moiety modified nucleotide comprises a linker between the capture moiety and a nucleobase of the nucleotide. In some embodiments, the capture moiety is covalently linked to the nucleobase via a linker of any suitable length. In some embodiments, the capture moiety is covalently linked to the nucleobase via a linker of 5 to 20 atoms in length. In some embodiments, the linker comprises an aliphatic chain. In some embodiments a linker comprises —$(CH_2)_n$—, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises —$(CH_2CH_2O)_n$—, wherein n is an integer from 1 to 20, inclusive. In some embodiments, a linker comprises —$(CH_2CH_2O)_n$—, wherein n is an integer from 1 to 10, inclusive. In certain embodiments, a linker comprises one or more arylenes. In some embodiments, a linker comprises one or more phenylenes (e.g., para-substituted phenylene). In certain embodiments, a linker comprises a chiral center. In certain embodiments, a linker comprises one or more phosphates, an aliphatic chain, a heteroaliphatic chain, and one or more amides (e.g., —C(═O)NH—).

In some embodiments, a capture moiety modified nucleotide is biotin-n-dNTP, wherein n is an integer from 5 to 20 representing the number of linker atoms between a carbonyl-group of the biotin moiety and the position of attachment on a nucleobase of the NTP.

In some embodiments, a binding partner is attached to an insoluble support. Thus, in some embodiments, the molecule of interest may be immobilized on an insoluble support through a selective binding interaction formed between a capture moiety and a binding partner of the capture moiety attached to the insoluble support.

In some embodiments, the insoluble support comprises a bead or other solid surface. For example, in some embodiments, the bead is a paramagnetic bead. The use of beads for isolation is well known in the art, and any suitable bead isolation method can be used with the techniques described herein. In some embodiments, beads can be useful for isolation in that molecules of interest can be attached to the beads, and the beads can be washed to remove solution components not attached to the beads, allowing for purification and isolation. In some embodiments, the beads can be separated from other components in the solution based on properties such as size, density, or dielectric, ionic, and magnetic properties.

In some embodiments, the insoluble support is a magnetic bead. Use of beads allows the derivatized nucleic acid capture moiety to be separated from a reaction mixture by centrifugation or filtration, or, in the case of magnetic beads, by application of a magnetic field. In some embodiments, magnetic beads can be introduced, mixed, removed, and released into solution using magnetic fields. In some embodiments, processes utilizing magnetic beads may be automated. In some embodiments, the beads can be functionalized using well known chemistry to provide a surface having suitable functionalization for attaching a binding partner of a capture moiety. Derivatization of surfaces to allow binding of the capture moiety is conventional in the art. For example, coating of surfaces with streptavidin allows binding of a biotinylated capture moiety. Coating of surfaces with streptavidin has been described in, for example, U.S. Pat. No. 5,374,524 to Miller. In some embodiments, solid surfaces other than beads may be used. In some embodiments, the solid surfaces can be planar surfaces, such as those used for hybridization microarrays, or the solid surfaces can be the packing of a separation column.

In some embodiments, a binding partner of a capture moiety may be attached to an insoluble support before, simultaneous with, or after binding the capture moiety. In some embodiments, it may be preferable to contact a capture moiety with a binding partner of the capture moiety while both are in solution. In such embodiments, the capture moiety:binding partner complex can then be immobilized on an insoluble support by contacting the complex with an appropriately derivatized surface. Thus, in some embodiments, the molecule of interest may be isolated through a complex formed between a capture moiety attached to the molecule of interest and a binding partner of the capture moiety.

In some embodiments, it may be desirable to attach the capture moiety to a nucleobase of a nucleotide. In this manner, the 3' end remains free to be optionally ligated to an adapter nucleic acid while the capture moiety is available to be captured by a binding partner. In some embodiments, the capture moiety modified nucleotide comprises a nucleobase selected from the group consisting of adenine, guanine, thymine, uracil, and cytosine, or a derivative thereof. For example, in some embodiments, the capture moiety modified nucleotide comprises an adenine nucleobase or derivative thereof. In some embodiments, the capture moiety is covalently linked to the adenine nucleobase or derivative thereof at position 5, 6, 7 or 8. In some embodiments, the capture moiety is covalently linked to the adenine nucleobase at position 7. A numbering scheme for an adenine ring is depicted in formula (II):

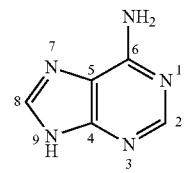

(II)

In some embodiments, it may be desirable to modify one or more positions on a nucleobase that is attached to a capture moiety. For example, in some embodiments, position 7 of the adenine nucleobase is a carbon atom. However, it should be appreciated that any atom capable of forming an additional covalent bond (e.g., C, O, N, S, etc.) may be substituted into a position on a nucleobase suitable for attachment of a capture moiety. In some embodiments, following capturing the adapter-ligated fragments, the library is subjected to amplification to enrich target nucleotide sequences.

Preparation of Nucleic Acids for Analysis

Aspects of the disclosure provide improved methods of determining the nucleotide sequence contiguous to a known target nucleotide sequence. Traditional sequencing methods generate sequence information randomly (e.g., "shotgun" sequencing) or between two known sequences which are used to design primers. In contrast, certain of the methods described herein, in some embodiments, allow for determining the nucleotide sequence (e.g., sequencing) upstream or downstream of a single region of known sequence with a high level of specificity and sensitivity.

In some embodiments, the disclosure provides a method of enriching specific nucleotide sequences prior to determining the nucleotide sequence using a next-generation sequencing technology. In some embodiments, methods provided herein can relate to enriching samples comprising deoxyribonucleic acid (DNA). In some embodiments, methods provided herein comprise: (a) adding one or more nucleotides to a 3' end of a double-stranded nucleic acid comprising a target nucleotide sequence, wherein at least one (e.g., 1, 2, 3, 4, 5 or more) of the one or more nucleotides is a capture moiety modified nucleotide; (b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double stranded nucleic acid in step (a); (c) capturing the ligation product by contacting the ligation product with a binding partner of a capture moiety of the capture moiety modified nucleotide; and (d) amplifying the ligation product by polymerase chain reaction using a first target-specific primer that specifically anneals to the target nucleotide sequence and a first adapter primer that specifically anneals to a complementary sequence of the adapter nucleic acid.

Figure 2:
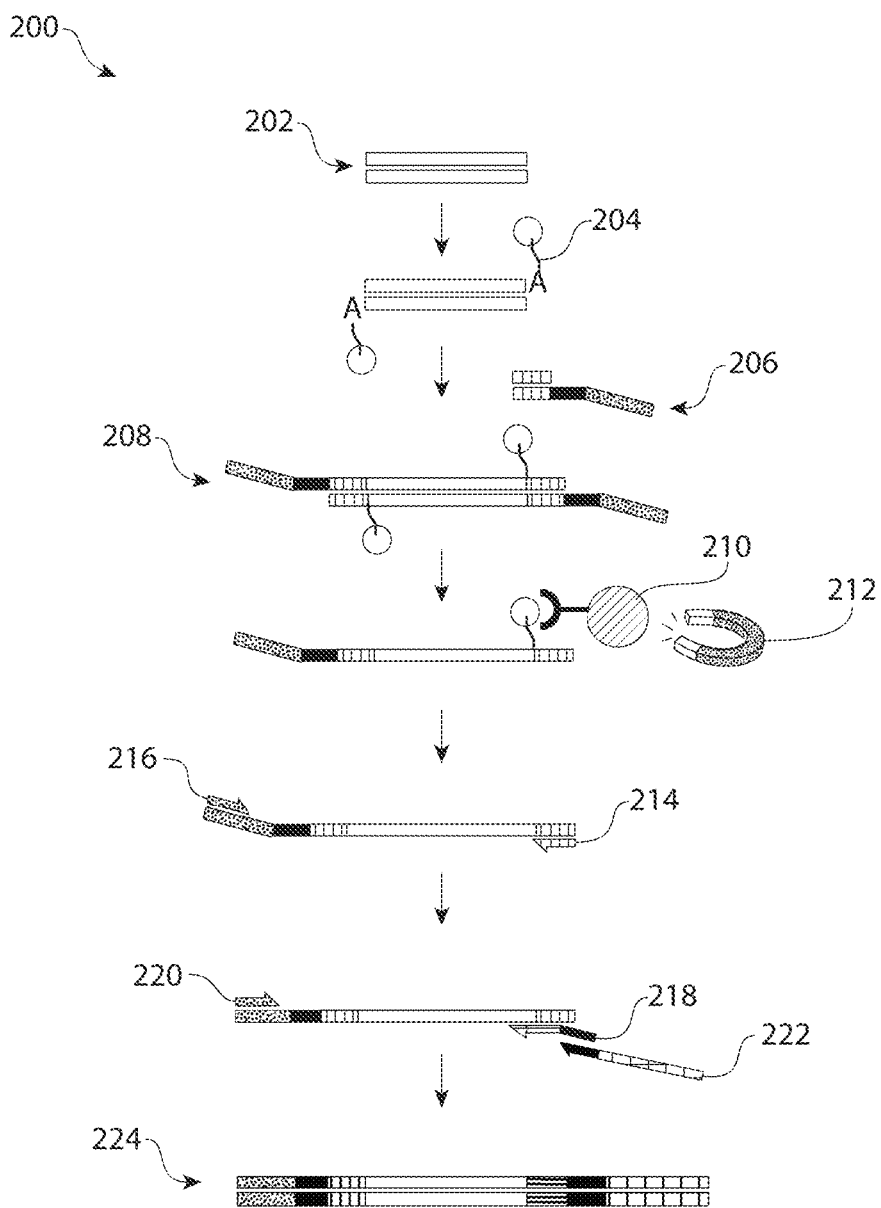
FIG. 2 is an illustration of a method of preparing a high-fidelity nucleic acid sample for analysis.

In some embodiments, the method further comprises: (e) amplifying an amplification product of step (d) by polymerase chain reaction using a second adapter primer and a second target-specific primer. For example, FIG. 2 depicts a non-limiting process 200 by which this embodiment can proceed. Double-stranded nucleic acid 202 comprising a target nucleotide sequence is tailed by adding one or more capture moiety modified nucleotides 204 to the 3' ends (e.g., 1, 2, 3, 4, 5 or more capture moiety modified nucleotides). The capture moiety labeled nucleic acid is ligated with an adapter 206 to generate an adapter-ligated library fragment 208. The adapter-ligated fragment is isolated by introducing a binding partner of the capture moiety, the former of which is attached to a magnetic support 210. Application of a magnetic field 212 isolated adapter-ligated nucleic acids from unligated adapter. The captured ligation product is subjected to a first round of PCR using a first target-specific primer 214 that specifically anneals to the target nucleotide sequence and a first adapter primer 216 that specifically anneals to a complementary sequence of the adapter nucleic acid. In this way, the first adapter primer 216 primes off of the strand generated by the first target-specific primer 214. A second round of PCR is conducted using a second target-specific primer 218 and a second adapter primer 220. As shown, the second target-specific primer 218 is nested relative to the first target-specific primer 214. Also as shown, the second target-specific primer is tailed with a 5' region that does not hybridize with the target nucleotide sequence. In a similar fashion to the first round of PCR, the second adapter primer 220 primes off of the strand generated by the second target-specific primer 218. In this second round of PCR, an additional primer 222 is included that contains (i) a 3' region that is identical to at least a portion of the tailed 5' region of the second target-specific primer 218 and (ii) a 5' region that can contain additional elements useful for sequencing, such as index or barcode sequences and primer binding sites. After the second adapter primer 220 generates a sense strand from the complementary strand generated by the second target-specific primer 218, the additional primer 222 then primes off of the now complementary sequence of the tailed region to generate the sequencing-ready product 224.

In some embodiments, the techniques described herein allow for the enrichment of target nucleotide sequences from a nucleic acid sample. In some embodiments, the nucleic acid sample comprises genomic DNA. In some embodiments, the nucleic acid sample comprises cDNA. In some embodiments, cDNA may be prepared by conducting a randomly-primed first strand synthesis reaction using a product of the randomly-primed first strand synthesis reaction as a template, wherein the RNA preparation comprises a target nucleotide sequence. In some embodiments, a nucleic acid sequencing library is prepared from an RNA preparation. For example, FIG. 3 generically depicts a process 300 by which a double-stranded nucleic acid library fragment is prepared from an RNA template.

As shown, an RNA template 302 is annealed with random primers 304 (e.g., random hexamers) under conditions suitable for hybridization. Following random priming, first strand cDNA synthesis is achieved by template-dependent extension using a reverse transcriptase enzyme to generate a DNA/RNA hybrid 306. The RNA strand of the DNA/RNA hybrid is enzymatically or chemically cleaved. The resulting fragments of RNA 308 that remain hybridized to the DNA strand 310 serve as primers for second strand cDNA synthesis via the action of a polymerase. In some embodiments, inactivation of the polymerase following second strand cDNA synthesis may be desirable, for example, to prevent 5'→3' and/or 3'→5' exonuclease activity during end repair. Following second strand cDNA synthesis, the double-stranded cDNA 312 is subjected to end repair to generate blunt ended, 5' phosphorylated cDNA 314. In some embodiments, SPRI cleanup (e.g., AMPure) is conducted following end repair. As subsequent steps in the process may involve adding a capture moiety modified nucleotide to a 3' end of the nucleic acid, it may be preferable to remove any residual dNTPs in the sample. Thus, any cleanup method capable of removing dNTPs from solution are envisioned to be suitable in this technique. In some embodiments, a capture moiety modified nucleotide may be added and/or incorporated into a nucleic acid at an earlier step of preparing the nucleic acids (e.g., fragmentation, random or specific priming, first strand synthesis, second strand synthesis, and/or end repair). In such embodiments, it may therefore be desirable to perform a cleanup step preceding the step of adding and/or incorporating the capture moiety modified nucleotide.

The blunt ended, 5' phosphorylated cDNA 314 is tailed with a biotin-labeled dATP 316 (biotin-11-ATP) comprising a thioate bond (e.g., a phosphorothioate bond) at its 3' ends and subjected to SPRI cleanup before being ligated with an adapter nucleic acid to generate an adapter-ligated library fragment 318. The inclusion of a crowding agent (20%) was shown to increase adapter ligation efficiency. The adapter-ligated fragment 318 is captured by introducing a streptavidin-coated paramagnetic bead 320. Once the non-covalent biotin-streptavidin complex has formed, application of a magnetic field 322 captures the adapter-ligated nucleic acids to isolate the desired product from unligated adapter.

Figure 3:
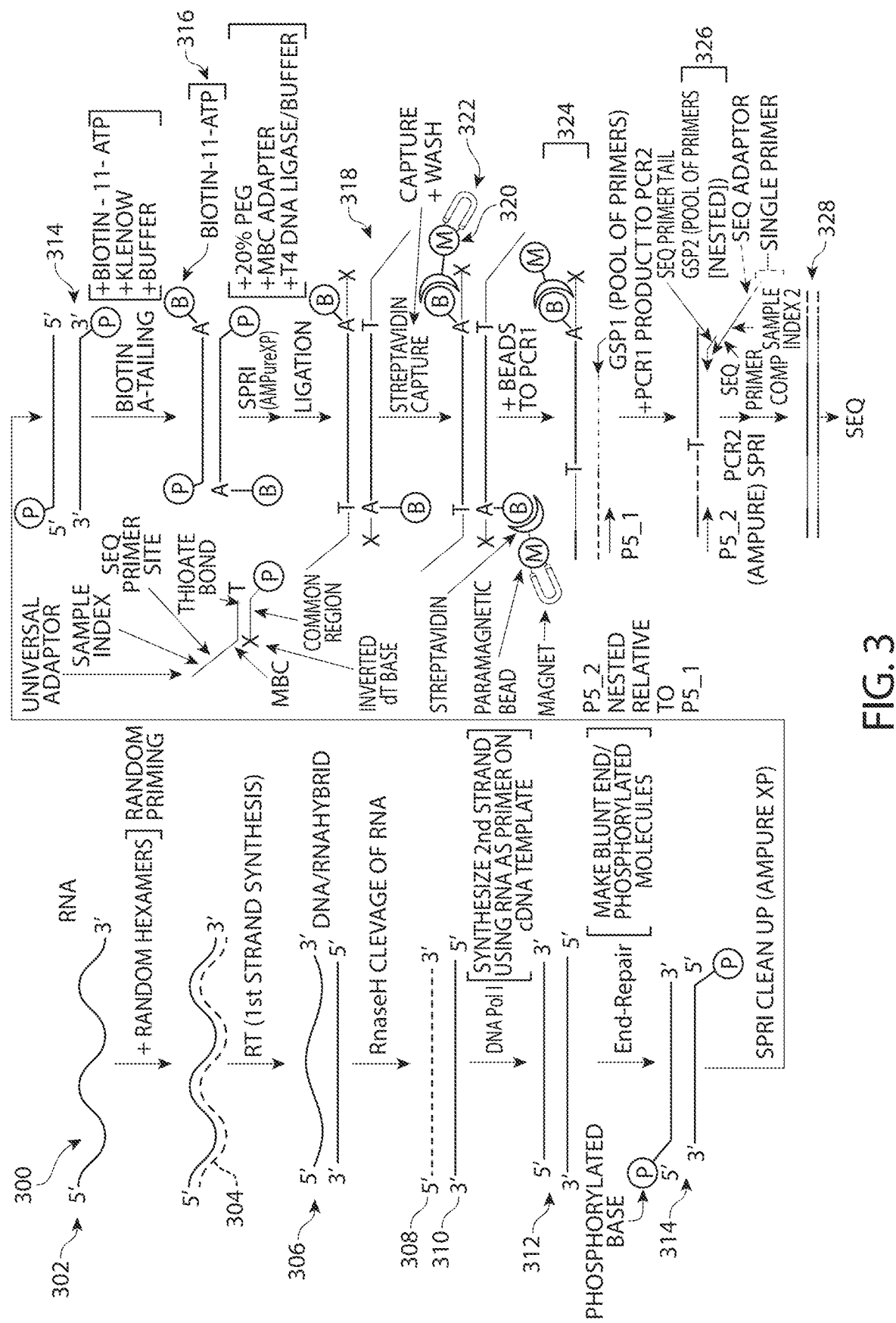
FIG. 3 depicts a process of generating a double-stranded cDNA sample using a template RNA strand.
Figure 4:
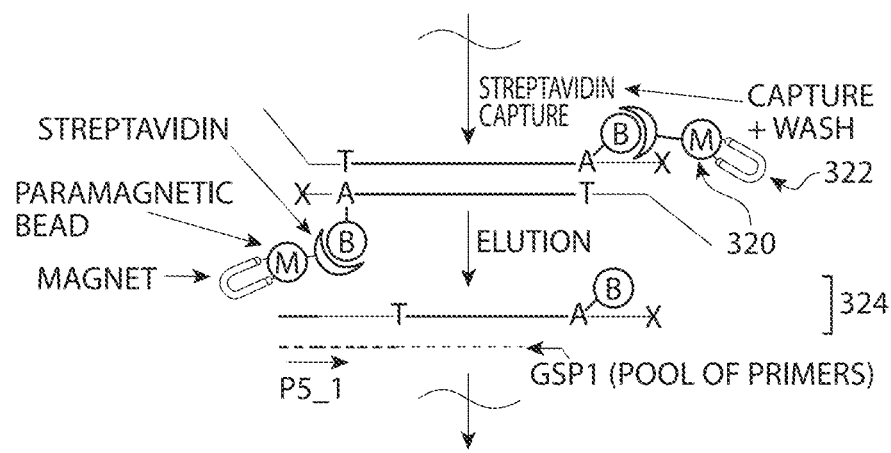
FIG. 4 depicts a process of generating a double-stranded cDNA sample using a template RNA strand, where captured ligation product is eluted from magnetic beads prior to amplification.

As shown in FIG. 3, in some embodiments, the captured adapter-ligated nucleic acid is subjected to a first round of PCR 324 in the form of a bead-immobilized product. In yet other embodiments, as shown in FIG. 4, the captured adapter-ligated nucleic acid is eluted from the paramagnetic bead 320 prior to first round PCR 324. Elution of captured adapter-ligated nucleic acids from the beads can be performed, by way of example and not limitation, using a chemical reagent and/or heat. In some embodiments, the chemical reagent is a base (e.g., NaOH). In some embodiments, captured adapter-ligated nucleic acid is eluted with a low concentration (e.g., less than 1 M, less than 0.5 M, less than 0.1 M, less than 0.05 M, less than 0.01 M, less than 0.001 M, less than 0.0001 M) of NaOH. In some embodiments, captured adapter-ligated nucleic acid is eluted with a low concentration of NaOH and heat.

The immobilized (e.g., as in FIG. 3) or eluted (e.g., as in FIG. 4) adapter-ligated nucleic acid is subjected to a first round of PCR 324 using a first gene-specific primer ("GSP1") that specifically anneals to the target nucleotide sequence and a first adapter primer ("P5_1") that specifically anneals to a complementary sequence of the adapter nucleic acid. In this way, P5_1 primes off of the strand generated by GSP1. As shown, in some embodiments, GSP1 (e.g., a first target-specific primer) is tailed with a 5' region that does not hybridize with the target nucleotide sequence. In some embodiments, a 5' tail region can prevent primer dimers, e.g., by having a sequence content that minimizes the occurrence of primer dimers. In some embodiments, GSP1 is not tailed with the 5' tailed region. As further shown in FIG. 3, a second round of PCR 326 is conducted using a second gene-specific primer ("GSP2") and a second adapter primer ("P5_2"). As shown, GSP2 is nested relative to GSP1. Also as shown, GSP2 is tailed with a 5' region that does not hybridize with the target nucleotide sequence. In a similar fashion to the first round of PCR, P5_2 primes off of the strand generated by GSP2. In this second round of PCR, an additional primer ("SINGLE PRIMER") is included that contains (i) a 3' region that is identical to at least a portion of the tailed 5' region of GSP2 and (ii) a 5' region that contains additional elements useful for sequencing, such as a sequencing primer binding site and a sample index. After P5_2 generates a sense strand from the complementary strand generated by GSP2, the additional primer then primes off of the now complementary sequence of the GSP2 tailed region to generate the sequencing-ready product 328.

Sample Purification

In some embodiments, target nucleic acids and/or amplification products thereof can be isolated from enzymes, primers, or buffer components before and/or after any appropriate step of a method. Any suitable methods for isolating nucleic acids may be used. In some embodiments, the isolation can comprise Solid Phase Reversible Immobilization (SPRI) cleanup. Methods for SPRI cleanup are well known in the art, e.g., Agencourt AMPure XP-PCR Purification (Cat No. A63880, Beckman Coulter; Brea, Calif.). In some embodiments, enzymes can be inactivated by heat treatment. In some embodiments, unlabeled dNTPs are removed by enzymatic treatment.

In some embodiments, unhybridized primers can be removed from a nucleic acid preparation using appropriate methods (e.g., purification, digestion, etc.). In some embodiments, a nuclease (e.g., exonuclease I) is used to remove primers from a preparation. In some embodiments, such nucleases are heat inactivated subsequent to primer digestion. Once the nucleases are inactivated, a further set of primers may be added together with other appropriate components (e.g., enzymes, buffers) to perform a further amplification reaction.

In some embodiments, steps of the methods provided herein optionally comprise an intervening sample purification step. In some embodiments, a sample purification step comprises a wash step. In some embodiments, a sample purification step comprises SPRI cleanup (e.g., AMPure). For example, a method of preparing nucleic acids for analysis can comprise: (a) preparing a cDNA by conducting a randomly-primed first strand synthesis reaction using an RNA preparation as a template and a second strand synthesis reaction using a product of the randomly-primed first strand synthesis reaction as a template, wherein the RNA preparation comprises a target nucleotide sequence; (b) end repairing the cDNA to produce a blunt-ended, double-stranded nucleic acid comprising the target nucleotide sequence; (c) immobilizing the blunt-ended, double-stranded nucleic acid on a paramagnetic substrate or surface; (d) washing the immobilized blunt-ended, double-stranded nucleic acid; (e) releasing the washed immobilized blunt-ended, double-stranded nucleic acid from the paramagnetic substrate or surface; (f) adding one or more nucleotides to the 3' end of the released blunt-ended, double-stranded nucleic acid; (g) ligating an adapter that comprises a ligatable duplex portion and an overhang sequence to the nucleic acid produced in step (f) to produce a ligation product, wherein the overhang sequence is complementary with the one or more nucleotides; (h) without washing the ligation product, amplifying the ligation product by polymerase chain reaction using a first target-specific primer that specifically anneals to the target nucleotide sequence and a first adapter primer that specifically anneals to a complementary sequence of the adapter nucleic acid; (i) amplifying an amplification product of step (h) by polymerase chain reaction using a second adapter primer and a second target-specific primer, wherein the second target-specific primer is nested relative to the first target-specific primer; (j) immobilizing the amplification product of step (i) to a paramagnetic substrate or surface; (k) washing the immobilized amplification product; and (l) releasing the washed immobilized amplification product from the paramagnetic substrate or surface. In some embodiments, steps of the methods provided herein optionally comprise adding one or more nucleotides to a nucleic acid, wherein at least one of the one or more nucleotides comprises a capture moiety, and capturing the nucleic acid via an interaction between the capture moiety and a binding partner of the capture moiety. For example, a method of preparing nucleic acids for analysis can comprise: (a) preparing a cDNA by conducting a randomly-primed first strand synthesis reaction using a nucleic acid preparation as a template and a second strand synthesis reaction using a product of the randomly-primed first strand synthesis reaction as a template, wherein the nucleic acid preparation comprises a target nucleotide sequence; (b) end repairing the cDNA to produce a blunt-ended, double-stranded nucleic acid comprising the target nucleotide sequence; (c) washing the blunt-ended, double-stranded nucleic acid; (d) adding one or more nucleotides to the 3' end of the nucleic acid washed in step (c), optionally wherein at least one of the one or more nucleotides is a capture moiety modified nucleotide; (e) washing the nucleic acid produced in step (d); (f) ligating an adapter nucleic acid that comprises a ligatable duplex portion and an overhang sequence to the nucleic acid washed in step (e) to produce a ligation product, wherein the overhang sequence is complementary with the one or more nucleotides; (g) amplifying the ligation product by polymerase chain reaction using a first target-specific primer that specifically anneals to the target nucleotide sequence and a first adapter primer that specifically anneals to a complementary sequence of the adapter nucleic acid; (h) amplifying an amplification product of step (g) by polymerase chain reaction using a second adapter primer and a second target-specific primer, wherein the second target-specific primer is nested relative to the first target-specific primer; and (j) washing the amplification product of step (h).

Nucleic Acid Adapter

As used herein, the term "nucleic acid adapter" or "adapter" refers to a nucleic acid molecule that may be ligated to a nucleic acid comprising a target nucleotide sequence to provide one or more elements useful during amplification and/or sequencing of the target nucleotide sequence. In some embodiments, an adapter is single-stranded. In some embodiments, an adapter is double-stranded. In some embodiments, a double-stranded adapter comprises a first ligatable duplex end and a second unpaired end. In some embodiments, an adapter comprises an amplification strand and a blocking strand. In some embodiments, the amplification strand comprises a 5' unpaired portion and a 3' duplex portion. In some embodiments, the amplification strand further comprises a 3' overhang. In some embodiments, the 3' overhang is a 3' T overhang. In some embodiments, the amplification strand comprises nucleotide sequences identical to a first and second adapter primer. In some embodiments, the blocking strand of the adapter comprises a 5' duplex portion and a non-extendable 3' portion. In some embodiments, the blocking strand further comprises a 3' unpaired portion. In some embodiments, the duplex portions of the amplification strand and the blocking strand are substantially complementary and the duplex portion is of sufficient length to remain in duplex form at the ligation temperature.

In some embodiments, the portion of the amplification strand that comprises a nucleotide sequence identical to a first and second adapter primer can be comprised, at least in part, by the 5' unpaired portion of the amplification strand.

In some embodiments, the adapter can have a "Y" shape, i.e., the second unpaired end comprises a 5' unpaired portion of an amplification strand and a 3' portion of a blocking strand. The 3' unpaired portion of the blocking strand can be shorter than, longer than, or equal in length to the 5' unpaired portion of the amplification strand. In some embodiments, the 3' unpaired portion of the blocking strand can be shorter than the 5' unpaired portion of the amplification strand.

Y-shaped adapters have the advantage that the unpaired portion of the blocking strand will not be subject to 3' extension during a PCR regimen.

In some embodiments, the blocking strand of the adapter can further comprise a 3' unpaired portion that is not substantially complementary to the 5' unpaired portion of the amplification strand, wherein the 3' unpaired portion of the blocking strand is not substantially complementary to or substantially identical to any of the primers. In some embodiments, the blocking strand can further comprise a 3' unpaired portion that does not specifically anneal to the 5' unpaired portion of the amplification strand at the annealing temperature, wherein the 3' unpaired portion of the blocking strand will not specifically anneal to any of the primers or the complements thereof at the annealing temperature. In some embodiments, an adapter nucleic acid comprises, at a minimum, a sample index sequence for multiplexing. However, in some embodiments, the adapter nucleic further comprises a random molecular barcode.

Amplification

Aspects of the present disclosure relate to techniques that may comprise one or more rounds of amplification. In some embodiments, a first round of amplification is conducted using a first target-specific primer and a first adapter primer.

As used herein, a "first target-specific primer" is an oligonucleotide comprising a nucleic acid sequence that can specifically anneal, under suitable annealing conditions, to a target nucleotide sequence of a template nucleic acid. During amplification, the first target-specific primer generates a strand that is complementary to its template, and this complementary strand is capable of being hybridized with a first adapter primer.

As used herein, a "first adapter primer" is an oligonucleotide comprising a nucleic acid sequence that can specifically anneal, under suitable annealing conditions, to a complementary sequence of an adapter nucleic acid. As the first adapter primer is therefore identical to at least a portion of the adapter, it anneals to the complementary strand generated by the first target specific-primer to allow amplification to proceed.

In some embodiments, in the first PCR amplification cycle of the first amplification step, a first target-specific primer can specifically anneal to a template strand of a nucleic acid comprising a target nucleotide sequence. In some embodiments, depending upon the orientation with which the first target-specific primer was designed, a sequence upstream or downstream of the target nucleotide sequence will be synthesized as a strand complementary to the template strand. In some embodiments, if, during the extension phase of PCR, the 5' end of a template strand terminates in a ligated adapter, the 3' end of the newly synthesized complementary strand will comprise sequence capable of hybridizing with a first adapter primer. In subsequent PCR amplification cycles, both the first target-specific primer and the first adapter primer will be able to specifically anneal to the appropriate strands of the target nucleic acid sequence and the sequence between the known nucleotide target sequence and the adapter can be amplified. In some embodiments, a second round of amplification is conducted using a second target-specific primer and a second adapter primer.

As used herein, a "second target-specific primer" is an oligonucleotide comprising a nucleic acid sequence that can specifically anneal, under suitable annealing conditions, to a portion of the target nucleotide sequence comprised by the amplicon resulting from a preceding amplification step. During amplification, the second target-specific primer generates a strand that is complementary to its template, and this complementary strand is capable of being hybridized with a second adapter primer.

As used herein, a "second adapter primer" is an oligonucleotide comprising a nucleic acid sequence that can specifically anneal, under suitable annealing conditions, to a complementary sequence of an adapter nucleic acid. As the first adapter primer is therefore identical to at least a portion of the adapter, it anneals to the complementary strand generated by the second target specific-primer to allow amplification to proceed.

In some embodiments, a second target-specific primer is nested relative to a first target-specific primer. In some embodiments, the use of nested adapter primers eliminates the possibility of producing final amplicons that are amplifiable (e.g., during bridge PCR or emulsion PCR) but cannot be sequenced, a situation that can arise during hemi-nested methods. In other situations, hemi-nested approaches using a primer identical to a sequencing primer can result in the carry-over of undesired amplification products from the first PCR step to the second PCR step and would ultimately yield artificial sequencing reads. In some embodiments, a second target-specific primer is nested with respect to a first target-specific primer by at least 1 nucleotide, e.g., by 1, 2, 3, 4, 5, 6, 7, 8, 9, 10, or more nucleotides. In some embodiments, a second target-specific primer is nested with respect to a first target-specific primer by about 5 nucleotides to about 10 nucleotides, by about 10 nucleotides to about 15 nucleotides, by about 15 nucleotides to about 20 nucleotides, or by about 20 nucleotides or more.

Among other aspects, techniques described herein may involve the use of one or more nested primers. In some embodiments, the use of nested primers may reduce non-specific binding in PCR products due to the amplification of unexpected primer binding sites. As used herein, the term "nested" is used to describe a positional relationship between the annealing site of a primer of a primer pair and the annealing site of another primer of another primer pair. For example, in some embodiments, a second primer is nested by 1, 2, 3 or more nucleotides relative to a first primer, meaning that it binds to a site on the template strand that is frame-shifted by 1, 2, 3 or more nucleotides.

In some embodiments, a second target-specific primer comprises a 3' portion that specifically anneals to a target nucleotide sequence and a 5' tail that does not anneal to the target nucleotide sequence. In some embodiments, the 5' tail comprises a nucleic acid sequence that is identical to a second sequencing primer. In some embodiments, multiple primers (e.g., one or more target specific primers and/or one or more adapter primers) present in a reaction can comprise identical 5' tail sequence portions.

In some embodiments, a 5' tail can be a GC-rich sequence. In some embodiments, a 5' tail sequence may comprise at least 50% GC content, at least 55% GC content, at least 60% GC content, at least 65% GC content, at least 70% GC content, at least 75% GC content, at least 80% GC content, or higher GC content. In some embodiments, a 5' tail sequence may comprise at least 60% GC content. In some embodiments, a 5' tail sequence may comprise at least 65% GC content.

In some embodiments, a second round of amplification includes a second target-specific primer comprising a 5' tail, a first adapter primer, and an additional primer. In some embodiments, the additional primer comprises a 3' portion that is identical to the 5' tail of the second target-specific primer. In some embodiments, the additional primer may comprise additional sequences 5' to the hybridization sequence that may include barcode, index, adapter sequences, or sequencing primer sites. In some embodiments, the additional primer is a generic sequencing adapter/index primer.

In some embodiments, the first and second target-specific primers are substantially complementary to the same strand of the target nucleic acid. In some embodiments, the portions of the first and second target-specific primers that specifically anneal to the known target sequence can comprise a total of at least 20 unique bases of the known target nucleotide sequence, e.g., 20 or more unique bases, 25 or more unique bases, 30 or more unique bases, 35 or more unique bases, 40 or more unique bases, or 50 or more unique bases. In some embodiments, the portions of the first and second target-specific primers that specifically anneal to the known target sequence can comprise a total of at least 30 unique bases of the known target nucleotide sequence.

In some embodiments, the first adapter primer can comprise a nucleic acid sequence identical to about the 20 5'-most bases of the amplification strand of the adapter and the second adapter primer can comprise a nucleic acid sequence identical to about 30 bases of the amplification strand of the adapter, with a 5' base that is at least 1 nucleotide 3' of the 5' terminus of the amplification strand.

In some embodiments, an adapter ligated nucleic acid (e.g., a ligation product) is minimal. In such embodiments, a first adapter primer may be used that contains a portion of the adapter nucleic sequence at its 3' end and then additional sequencer-important information at its 5' end. In such embodiments, a second adapter primer may be used that contains, at its 3' end, the 5' end of the first adapter primer. In such embodiments, the second adapter primer may also have a nucleotide sequence that permits sequencing at its 5' end. In such embodiments, it is possible to produce, using PCR, a library that is sequencer compatible.

Primers

In some embodiments, primers (e.g., first and second target-specific primers and first and second adapter primers) are designed such that they will specifically anneal to their complementary sequences at an annealing temperature of from about 61 to 72° C., e.g., from about 61 to 69° C., from about 63 to 69° C., from about 63 to 67° C., from about 64 to 66° C. In some embodiments, primers are designed such that they will specifically anneal to their complementary sequences at an annealing temperature of less than 72° C. In some embodiments, primers are designed such that they will specifically anneal to their complementary sequences at an annealing temperature of less than 70° C. In some embodiments, primers are designed such that they will specifically anneal to their complementary sequences at an annealing temperature of less than 68° C. In some embodiments, primers are designed such that they will specifically anneal to their complementary sequences at an annealing temperature of about 65° C. In some embodiments, systems provided herein are configured to alter vessel temperature (e.g., by cycling between different temperature ranges) to facilitate primer annealing.

In some embodiments, the portions of the target-specific primers that specifically anneal to the known target nucleotide sequence will anneal specifically at a temperature of about 61 to 72° C., e.g., from about 61 to 69° C., from about 63 to 69° C., from about 63 to 67° C., from about 64 to 66° C. In some embodiments, the portions of the target-specific primers that specifically anneal to the known target nucleotide sequence will anneal specifically at a temperature of about 65° C. in a PCR buffer.

Nucleic Acid Extension, Amplification, and PCR

In some embodiments, methods described herein comprise an extension regimen or step. In such embodiments, extension may proceed from one or more hybridized random primers, using the nucleic acid molecules which the primers are hybridized to as templates. Extension steps are described herein. In some embodiments, one or more random primers can hybridize to substantially all of the nucleic acids in a sample, many of which may not comprise a target nucleotide sequence. Accordingly, in some embodiments, extension of random primers may occur due to hybridization with templates that do not comprise a target nucleotide sequence.

In some embodiments, methods described herein may involve a polymerase chain reaction (PCR) amplification regimen, involving one or more amplification cycles. Amplification steps of the methods described herein can each comprise a PCR amplification regimen, i.e., a set of polymerase chain reaction (PCR) amplification cycles. As used herein, the term "amplification regimen" refers to a process of specifically amplifying (increasing the abundance of) a nucleic acid of interest. In some embodiments, exponential amplification occurs when products of a previous polymerase extension serve as templates for successive rounds of extension. In some embodiments, a PCR amplification regimen according to methods disclosed herein may comprise at least one, and in some cases at least 5 or more iterative cycles. In some embodiments, each iterative cycle comprises steps of: 1) strand separation (e.g., thermal denaturation); 2) oligonucleotide primer annealing to template molecules; and 3) nucleic acid polymerase extension of the annealed primers. In should be appreciated that any suitable conditions and times involved in each of these steps may be used. In some embodiments, conditions and times selected may depend on the length, sequence content, melting temperature, secondary structural features, or other factors relating to the nucleic acid template and/or primers used in the reaction. In some embodiments, an amplification regimen according to methods described herein is performed in a thermal cycler, many of which are commercially available. In some embodiments, methods described herein can comprise linear amplification. For example, in some embodiments, amplification steps performed using nested primers may be performed using linear amplification. In some embodiments, amplification may be conducted using nucleic acid sequence-based amplification (NASBA). For example, in some embodiments, amplification comprises a T7-mediated NASBA reaction.

In some embodiments, a nucleic acid extension reaction involves the use of a nucleic acid polymerase. As used herein, the phrase "nucleic acid polymerase" refers to an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and are commercially available. One group of nucleic acid polymerases are thermostable, i.e., they retain function after being subjected to temperatures sufficient to denature annealed strands of complementary nucleic acids, e.g., 94° C., or sometimes higher. A non-limiting example of a protocol for amplification involves using a polymerase (e.g., Phoenix Taq, VeraSeq) under the following conditions: 98° C. for 30 s, followed by 14-22 cycles comprising melting at 98° C. for 10 s, followed by annealing at 68° C. for 30 s, followed by extension at 72° C. for 3 min, followed by holding of the reaction at 4° C. However, other appropriate reaction conditions may be used. In some embodiments, annealing/extension temperatures may be adjusted to account for differences in salt concentration (e.g., 3° C. higher to higher salt concentrations). In some embodiments, slowing the ramp rate (e.g., 1° C./s, 0.5° C./s, 0.28° C./s, 0.1° C./s or slower), for example, from 98° C. to 65° C., improves primer performance and coverage uniformity in highly multiplexed samples. In some embodiments, systems provided herein are configured to alter vessel temperature (e.g., by cycling between different temperature ranges, having controlled ramp up or down rates) to facilitate amplification.

In some embodiments, a nucleic acid polymerase is used under conditions in which the enzyme performs a template-dependent extension. In some embodiments, the nucleic acid polymerase is DNA polymerase I, Taq polymerase, Phoenix Taq polymerase, Phusion polymerase, T4 polymerase, T7 polymerase, Klenow fragment, Klenow exo-, phi29 polymerase, AMV reverse transcriptase, M-MuLV reverse transcriptase, HIV-1 reverse transcriptase, VeraSeq ULtra polymerase, VeraSeq HF 2.0 polymerase, EnzScript, or another appropriate polymerase. In some embodiments, a nucleic acid polymerase is not a reverse transcriptase. In some embodiments, a nucleic acid polymerase acts on a DNA template. In some embodiments, the nucleic acid polymerase acts on an RNA template. In some embodiments, an extension reaction involves reverse transcription performed on an RNA to produce a complementary DNA molecule (RNA-dependent DNA polymerase activity). In some embodiments, a reverse transcriptase is a mouse moloney murine leukemia virus (M-MLV) polymerase, AMV reverse transcriptase, RSV reverse transcriptase, HIV-1 reverse transcriptase, HIV-2 reverse transcriptase, or another appropriate reverse transcriptase.

In some embodiments, a nucleic acid amplification reaction involves cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. In some embodiments, strand separation according to methods described herein is achieved by heating the nucleic acid sample above its melting temperature ($T_m$). In some embodiments, for a sample containing nucleic acid molecules in a reaction preparation suitable for a nucleic acid polymerase, heating to 94° C. is sufficient to achieve strand separation. In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCl), and a carrier (e.g., 0.01 to 0.5% BSA). A non-limiting example of a suitable buffer comprises 50 mM KCl, 10 mM Tris-HCl (pH 8.8 at 25° C.), 0.5 to 3 mM $MgCl_2$, and 0.1% BSA. A further non-limiting example of a suitable buffer comprises 50 mM KCl, 10 mM Tris-HCl (pH 8.8 at 25° C.), 0.5 to 5 mM (e.g., approximately 0.5 mM, approximately 1 mM, approximately 2 mM, approximately 3 mM, approximately 4 mM, approximately 5 mM) $MgCl_2$, and 0.1% BSA.

In some embodiments, a nucleic acid amplification involves annealing primers to nucleic acid templates having a strands characteristic of a target nucleic acid. In some embodiments, a strand of a target nucleic acid can serve as a template nucleic acid. As used herein, the term "anneal" refers to the formation of one or more complementary base pairs between two nucleic acids. In some embodiments, annealing involves two complementary or substantially complementary nucleic acid strands hybridizing together. In some embodiments, in the context of an extension reaction, annealing involves the hybridization of primer to a template such that a primer extension substrate for a template-dependent polymerase enzyme is formed. In some embodiments, conditions for annealing (e.g., between a primer and nucleic acid template) may vary based of the length and sequence of a primer. In some embodiments, conditions for annealing are based upon a $T_m$ (e.g., a calculated $T_m$) of a primer. In some embodiments, an annealing step of an extension regimen involves reducing the temperature following a strand separation step to a temperature based on the $T_m$ (e.g., a calculated $T_m$) for a primer, for a time sufficient to permit such annealing. In some embodiments, a $T_m$ can be determined using any of a number of algorithms (e.g., OLIGO™ (Molecular Biology Insights Inc. Colorado) primer design software and VENTRO NTI™ (Invitrogen, Inc. California) primer design software and programs available on the internet, including Primer3, Oligo Calculator, and NetPrimer (Premier Biosoft; Palo Alto, Calif.; and freely available on the world wide web (e.g., at premierbiosoft.com/netprimer/netprlaunch/Help/xnetprlaunch.html)). In some embodiments, the $T_m$ of a primer can be calculated using the following formula, which is used by NetPrimer software and is described in more detail in Frieir, et al. PNAS 1986 83:9373-9377 which is incorporated by reference herein in its entirety.

$$T_m = \Delta H/(\Delta S + R^* \ln(C/4)) + 16.6 \log([K^+]/(1+0.7[K^+])) - 273.15$$

wherein: $\Delta H$ is enthalpy for helix formation; $\Delta S$ is entropy for helix formation; R is molar gas constant (1.987 cal/° C.*mol); C is the nucleic acid concentration; and $[K^+]$ is salt concentration. For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can, for example, temperatures more than 5° C. below the predicted $T_m$ (e.g., 6° C. below, 8° C. below, 10° C. below or lower). In some embodiments, the closer an annealing temperature is to the $T_m$, the more specific is the annealing. In some embodiments, the time used for primer annealing during an extension reaction (e.g., within the context of a PCR amplification regimen) is determined based, at least in part, upon the volume of the reaction (e.g., with larger volumes involving longer times). In some embodiments, the time used for primer annealing during an extension reaction (e.g., within the context of a PCR amplification regimen) is determined based, at least in part, upon primer and template concentrations (e.g., with higher relative concentrations of primer to template involving less time than lower relative concentrations). In some embodiments, depending upon volume and relative primer/template concentration, primer annealing steps in an extension reaction (e.g., within the context of an amplification regimen) can be in the range of 1 second to 5 minutes, 10 seconds to 2 minutes, or 30 seconds to 2 minutes. As used herein, "substantially anneal" refers to an extent to which complementary base pairs form between two nucleic acids that, when used in the context of a PCR amplification regimen, is sufficient to produce a detectable level of a specifically amplified product.

As used herein, the term "polymerase extension" refers to template-dependent addition of at least one complementary nucleotide, by a nucleic acid polymerase, to the 3' end of a primer that is annealed to a nucleic acid template. In some embodiments, polymerase extension adds more than one nucleotide, e.g., up to and including nucleotides corresponding to the full length of the template. In some embodiments, conditions for polymerase extension are based, at least in part, on the identity of the polymerase used. In some embodiments, the temperature used for polymerase extension is based upon the known activity properties of the enzyme. In some embodiments, in which annealing temperatures are below the optimal temperatures for the enzyme, it may be acceptable to use a lower extension temperature. In some embodiments, enzymes may retain at least partial activity below their optimal extension temperatures. In some embodiments, a polymerase extension (e.g., performed with thermostable polymerases such as Taq polymerase and variants thereof) is performed at 65° C. to 75° C. or 68° C. to 72° C. In some embodiments, methods provided herein involve polymerase extension of primers that are annealed to nucleic acid templates at each cycle of a PCR amplification regimen. In some embodiments, a polymerase extension is performed using a polymerase that has relatively strong strand displacement activity. In some embodiments, polymerases having strong strand displacement are useful for preparing nucleic acids for purposes of detecting fusions (e.g., 5' fusions). In some embodiments, polymerases having exonuclease activity (e.g., Taq polymerase) are useful for producing long library fragments.

In some embodiments, primer extension is performed under conditions that permit the extension of annealed oligonucleotide primers. As used herein, the term "conditions that permit the extension of an annealed oligonucleotide such that extension products are generated" refers to the set of conditions (e.g., temperature, salt and co-factor concentrations, pH, and enzyme concentration) under which a nucleic acid polymerase catalyzes primer extension. In some embodiments, such conditions are based, at least in part, on the nucleic acid polymerase being used. In some embodiments, a polymerase may perform a primer extension reaction in a suitable reaction preparation.

In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCl), a carrier (e.g., 0.01 to 0.5% BSA), and one or more NTPs (e.g, 10 to 200 µM of each of dATP, dTTP, dCTP, and dGTP). A non-limiting set of conditions is 50 mM KCl, 10 mM Tris-HCl (pH 8.8 at 25° C.), 0.5 to 3 mM $MgCl_2$, 200 µM each dNTP, and 0.1% BSA at 72° C., under which a polymerase (e.g., Taq polymerase) catalyzes primer extension.

In some embodiments, a suitable reaction preparation contains one or more salts (e.g., 1 to 100 mM KCl, 0.5 to 5 mM $MgCl_2$), at least one buffering agent (e.g., 1 to 20 mM Tris-HCl), a carrier (e.g., 0.01 to 0.5% BSA), and one or more NTPs (e.g, 50 to 350 µM of each of dATP, dTTP, dCTP, and dGTP). A non-limiting set of conditions is 50 mM KCl, 10 mM Tris-HCl (pH 8.8 at 25° C.), 3 mM $MgCl_2$, 200 µM each dNTP, and 0.1% BSA at 72° C., under which a polymerase (e.g., Taq polymerase) catalyzes primer extension. A further non-limiting set of conditions is 50 mM KCl, 10 mM Tris-HCl (pH 8.8 at 25° C.), 3 mM $MgCl_2$, 266 µM dATP, 200 µM dCTP, 133 µM dGTP, 200 µM dTTP, and 0.1% BSA at 72° C., under which a polymerase (e.g., Taq polymerase) catalyzes primer extension.

In some embodiments, conditions for initiation and extension may include the presence of one, two, three or four different deoxyribonucleoside triphosphates (e.g., selected from dATP, dTTP, dCTP, and dGTP) and a polymerization-inducing agent such as DNA polymerase or reverse transcriptase, in a suitable buffer. In some embodiments, a "buffer" may include solvents (e.g., aqueous solvents) plus appropriate cofactors and reagents which affect pH, ionic strength, etc. In some embodiments, the two, three or four different deoxyribonucleoside triphosphates are present in equimolar, or approximately equimolar, concentrations. In some embodiments, the two, three or four different deoxyribonucleoside triphosphates are present in different concentrations, which have been experimentally determined to be suitable to a particular implementation of the technology.

In some embodiments, nucleic acid amplification involves up to 5, up to 10, up to 20, up to 30, up to 40 or more rounds (cycles) of amplification. In some embodiments, nucleic acid amplification may comprise a set of cycles of a PCR amplification regimen from 5 cycles to 20 cycles in length. In some embodiments, an amplification step may comprise a set of cycles of a PCR amplification regimen from 10 cycles to 20 cycles in length. In some embodiments, each amplification step can comprise a set of cycles of a PCR amplification regimen from 12 cycles to 16 cycles in length. In some embodiments, an annealing temperature can be less than 70° C. In some embodiments, an annealing temperature can be less than 72° C. In some embodiments, an annealing temperature can be about 65° C. In some embodiments, an annealing temperature can be from about 61 to about 72° C.

In various embodiments, methods and compositions described herein relate to performing a PCR amplification regimen with one or more of the types of primers described herein. As used herein, "primer" refers to an oligonucleotide capable of specifically annealing to a nucleic acid template and providing a 3' end that serves as a substrate for a template-dependent polymerase to produce an extension product which is complementary to the template. In some embodiments, a primer is single-stranded, such that the primer and its complement can anneal to form two strands. Primers according to methods and compositions described herein may comprise a hybridization sequence (e.g., a sequence that anneals with a nucleic acid template) that is less than or equal to 300 nucleotides in length, e.g., less than or equal to 300, or 250, or 200, or 150, or 100, or 90, or 80, or 70, or 60, or 50, or 40, or 30 or fewer, or 20 or fewer, or 15 or fewer, but at least 6 nucleotides in length. In some embodiments, a hybridization sequence of a primer may be 6 to 50 nucleotides in length, 6 to 35 nucleotides in length, 6 to 20 nucleotides in length, 10 to 25 nucleotides in length.

Any suitable method may be used for synthesizing oligonucleotides and primers. In some embodiments, commercial sources offer oligonucleotide synthesis services suitable for providing primers for use in methods and compositions described herein (e.g., INVITROGEN™ Custom DNA Oligos (Life Technologies, Grand Island, N.Y.) or custom DNA Oligos from Integrated DNA Technologies (Coralville, Iowa)).

Target Nucleic Acid

As used herein, the terms "target nucleic acid" and "nucleic acid comprising a target nucleotide sequence" refer to a nucleic acid molecule of interest (e.g., a nucleic acid to be prepared for analysis). In some embodiments, a target nucleic acid comprises both a target nucleotide sequence (e.g., a known or predetermined nucleotide sequence) and an adjacent nucleotide sequence that is to be determined (which may be referred to as an unknown sequence). A target nucleic acid can be of any appropriate length. In some embodiments, a target nucleic acid is double-stranded. In some embodiments, a target nucleic acid is DNA. In some embodiments, a target nucleic acid comprises genomic or chromosomal DNA (gDNA). In some embodiments, a target nucleic acid comprises complementary DNA (cDNA). In some embodiments, a target nucleic acid is single-stranded. In some embodiments, a target nucleic acid comprises RNA (e.g., mRNA, rRNA, tRNA, cfDNA, cfRNA, long non-coding RNA, microRNA).

Many of the sequencing methods suitable for use in the methods described herein provide sequencing runs with optimal read lengths of tens to hundreds of nucleotide bases (e.g., Ion Torrent technology can produce read lengths of 200-400 bp). Target nucleic acids comprised, for example, by genomic DNA or mRNA, can be comprised by nucleic acid molecules which are substantially longer than this optimal read length. In order for the amplified nucleic acid portion resulting from the second amplification step to be of a suitable length (e.g., up to 100 bp, 200 bp, 300 bp, 400 bp, 500 bp, 1 kb, 2 kb) for use in a particular sequencing technology, the average distance between the known target nucleotide sequence and an end of the target nucleic acid to which the adapter can be ligated should be as close to the optimal read length of the selected technology as possible. For example, if the optimal read-length of a given sequencing technology is 200 bp, then the nucleic acid molecules amplified in accordance with the methods described herein should have an average length of about 400 bp or less. However, it should be appreciated that, in some embodiments, techniques described herein may be implemented when nucleic acid molecules exceed 400 bp in length. For example, in some embodiments, nucleic acid fragments can be approximately 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides.

Target nucleic acids comprised by, e.g., genomic DNA or mRNA, can be sheared, e.g., mechanically or enzymatically sheared, to generate fragments of any desired size. Non-limiting examples of mechanical shearing processes include sonication, nebulization, and AFA™ shearing technology available from Covaris (Woburn, Mass.). In some embodiments, a target nucleic acid comprised by genomic DNA can be mechanically sheared by sonication.

In some embodiments, when the target nucleic acid is comprised by RNA, the sample can be subjected to a reverse transcriptase regimen to generate a DNA template. In some embodiments, the DNA template can then be sheared. In some embodiments, the DNA template is not sheared. For example, in some embodiments, the concentration of primers used during a reverse transcriptase regimen can be adjusted such that the product cDNA is of an appropriate "fragmented" length. In some embodiments, target RNA can be sheared before performing the reverse transcriptase regimen. In some embodiments, a sample comprising target RNA can be used in the methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers; and by subjecting the nucleic acid to end-repair, phosphorylation, and adenylation.

In some embodiments, a target nucleotide sequence can be comprised by a gene rearrangement. The methods described herein are suited for determining the presence and/or identity of a gene rearrangement as the identity of only one half of the gene rearrangement must be previously known (i.e., the half of the gene rearrangement which is to be targeted by the gene-specific primers). In some embodiments, the gene rearrangement can comprise an oncogene. In some embodiments, the gene rearrangement can comprise a fusion oncogene. In some embodiments, the gene rearrangement can comprise a V(D)J recombination product.

As used herein, the term "known target nucleotide sequence" or "target nucleotide sequence" refers to a portion of a target nucleic acid for which the sequence (e.g., the identity and order of the nucleotide bases of the nucleic acid) is known. For example, in some embodiments, a known target nucleotide sequence is a nucleotide sequence of a nucleic acid that is known or that has been determined in advance of an interrogation of an adjacent unknown sequence of the nucleic acid. A known target nucleotide sequence can be of any appropriate length.

In some embodiments, a target nucleotide sequence (e.g., a known target nucleotide sequence) has a length of 10 or more nucleotides, 30 or more nucleotides, 40 or more nucleotides, 50 or more nucleotides, 100 or more nucleotides, 200 or more nucleotides, 300 or more nucleotides, 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides. In some embodiments, a target nucleotide sequence (e.g., a known target nucleotide sequence) has a length in the range of 10 to 100 nucleotides, 10 to 500 nucleotides, 10 to 1000 nucleotides, 100 to 500 nucleotides, 100 to 1000 nucleotides, 500 to 1000 nucleotides, 500 to 5000 nucleotides.

In some embodiments, methods are provided herein for determining sequences of contiguous (or adjacent) portions of a nucleic acid. As used herein, the term "nucleotide sequence contiguous to" refers to a nucleotide sequence of a nucleic acid molecule (e.g., a target nucleic acid) that is immediately upstream or downstream of another nucleotide sequence (e.g., a known nucleotide sequence). In some embodiments, a nucleotide sequence contiguous to a known target nucleotide sequence may be of any appropriate length. In some embodiments, a nucleotide sequence contiguous to a known target nucleotide sequence comprises 1 kb or less of nucleotide sequence, e.g., 1 kb or less of nucleotide sequence, 750 bp or less of nucleotide sequence, 500 bp or less of nucleotide sequence, 400 bp or less of nucleotide sequence, 300 bp or less of nucleotide sequence, 200 bp or less of nucleotide sequence, 100 bp or less of nucleotide sequence. In some embodiments, in which a sample comprises different target nucleic acids comprising a known target nucleotide sequence (e.g., a cell in which a known target nucleotide sequence occurs multiple times in its genome, or on separate, non-identical chromosomes), there may be multiple sequences which comprise "a nucleotide sequence contiguous to" the known target nucleotide sequence. As used herein, the term "determining a (or the) nucleotide sequence," refers to determining the identity and relative positions of the nucleotide bases of a nucleic acid.

In some embodiments, a known target nucleic acid can contain a fusion sequence resulting from a gene rearrangement. In some embodiments, methods described herein are suited for determining the presence and/or identity of a gene rearrangement. In some embodiments, the identity of one portion of a gene rearrangement is previously known (e.g., the portion of a gene rearrangement that is to be targeted by the gene-specific primers) and the sequence of the other portion may be determined using methods disclosed herein. In some embodiments, a gene rearrangement can involve an oncogene. In some embodiments, a gene rearrangement can comprise a fusion oncogene.

Molecular Barcodes and Index Sequences

In some embodiments, primers and/or adapters may contain additional sequences such as an identifier sequence (e.g., a barcode, an index), sequencing primer hybridization sequences (e.g., Rd1), and adapter sequences. In some embodiments the adapter sequences are sequences used with a next generation sequencing system. In some embodiments, the adapter sequences are P5 and P7 sequences for Illumina-based sequencing technology. In some embodiments, the adapter sequence are P1 and A compatible with Ion Torrent sequencing technology.

In some embodiments, as used herein, "barcode," "molecular barcode," and "molecular barcode tag" may be used interchangeably, and generally refer to a region of an adapter nucleic acid that is useful as an identifier for the specific nucleic acid to which it is ligated. In some embodiments, a molecular barcode comprises a randomized nucleic acid sequence that provides a unique identifier for the nucleic acid to which it is ligated. In some embodiments, a molecular barcode may be used to identify unique fragments and "de-duplicate" the sequencing reads from a sample. In some embodiments, a molecular barcode may be used to identify and remove PCR duplicates. In some embodiments, a molecular barcode may be 2 to 25 nucleotides in length, 2 to 15 nucleotides in length, 2 to 10 nucleotides in length, 2 to 6 nucleotides in length. In some embodiments, a molecular barcode comprises at least 2, 3, 4, 5, 6, 7, 8, 9, 10, 11, 12, 13, 14, 15, 16, 17, 18, 19, 20, 21, 22, 23, 24, or at least 25 nucleotides. In some embodiments, a molecular barcode comprises 8 nucleotides.

In some embodiments, as used herein, "index," "index sequence," "index region," and "sample index" may be used interchangeably, and generally refer to a region of an adapter nucleic acid that is useful as an identifier for the population to which the ligated nucleic acid belongs. In some embodiments, an index comprises a fixed nucleic acid sequence that may be used to identify a collection of sequences belonging to a common library. For example, an index may be used to identify a sample that corresponds to a nucleic acid. In some embodiments, an index may be used, for example, as a source identifier, location identifier, date or time identifier (e.g., date or time of sampling or processing), or other identifier of a nucleic acid relating to a shared or common property (e.g., common among other nucleic acids of a library). In some embodiments, such index sequences are useful for identifying different aspects of a nucleic acid that are present in a population of nucleic acids. In some embodiments, index sequences may provide a source or location identifier for a target nucleic acid. For example, an index sequence may serve to identify a patient from whom a nucleic acid is obtained. In some embodiments, index sequences enable sequencing of multiple different samples on a single reaction (e.g., performed in a single flow cell). In some embodiments, an index sequence can be used to orientate a sequence imager for purposes of detecting individual sequencing reactions. In some embodiments, an index sequence may be 2 to 25 nucleotides in length, 2 to 15 nucleotides in length, 2 to 10 nucleotides in length, 2 to 6 nucleotides in length. In some embodiments, an index comprises at least 2, 3, 4, 5, 6, 7, 8, 9, 10, 11, 12, 13, 14, 15, 16, 17, 18, 19, 20, 21, 22, 23, 24, or at least 25 nucleotides.

In some embodiments, when a population of tailed random primers is used in accordance with methods described herein, multiple distinguishable amplification products can be present after amplification. In some embodiments, because tailed random primers hybridize at various positions throughout nucleic acid molecules of a sample, a set of target-specific primers can hybridize (and amplify) the extension products created by more than 1 hybridization event, e.g., one tailed random primer may hybridize at a first distance (e.g., 100 nucleotides) from a target-specific primer hybridization site, and another tailed random primer can hybridize at a second distance (e.g., 200 nucleotides) from a target-specific primer hybridization site, thereby resulting in two amplification products (e.g., a first amplification product comprising about 100 bp and a second amplification product comprising about 200 bp). In some embodiments, these multiple amplification products can each be sequenced using next generation sequencing technology. In some embodiments, sequencing of these multiple amplification products is advantageous because it provides multiple overlapping sequence reads that can be compared with one another to detect sequence errors introduced during amplification or sequencing processes. In some embodiments, individual amplification products (e.g., derived from a single molecule) can be aligned and where they differ in the sequence present at a particular base, an artifact or error of PCR and/or sequencing may be present.

DNA Shearing/Fragmentation

The nucleic acid molecules described herein can be sheared (e.g., mechanically or enzymatically sheared, sheared via nebulizer) to generate fragments of any desired size. Non-limiting examples of mechanical shearing processes include sonication, nebulization, and AFA™ shearing technology available from Covaris (Woburn, Mass.). In some embodiments, a nucleic acid can be mechanically sheared by sonication. In some embodiments, a target nucleic acid is not sheared or digested. In some embodiments, nucleic acid products of preparative steps (e.g., extension products, amplification products) are not sheared or enzymatically digested.

In some embodiments, when a target nucleotide sequence comprises RNA, the sample can be subjected to a reverse transcriptase regimen to generate a DNA template and the DNA template can then be sheared. In some embodiments, target RNA can be sheared before performing a reverse transcriptase regimen. In some embodiments, a sample comprising target RNA can be used in methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers.

Sequencing

In some aspects, the technology described herein relates to methods of enriching nucleic acid samples for oligonucleotide sequencing. In some embodiments, the sequencing can be performed by a next-generation sequencing method. As used herein, "next-generation sequencing" refers to oligonucleotide sequencing technologies that have the capacity to sequence oligonucleotides at speeds above those possible with conventional sequencing methods (e.g., Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ION Torrent); DNA nanoball sequencing (Complete Genomics); and technologies available from Pacific Biosciences, Intelligen Biosystems, and Oxford Nanopore Technologies. In some embodiments, the sequencing primers can comprise portions compatible with the selected next-generation sequencing method. Next-generation sequencing technologies and the constraints and design parameters of associated sequencing primers are well known in the art (see, e.g., Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. No. 7,282,337; U.S. Pat. No. 7,279,563; U.S. Pat. No. 7,226,720; U.S. Pat. No. 7,220,549; U.S. Pat. No. 7,169,560; U.S. Pat. No. 6,818,395; U.S. Pat. No. 6,911,345; US Pub. Nos. 2006/0252077; 2007/0070349; and 20070070349; which are incorporated by reference herein in their entireties).

In some embodiments, the sequencing step relies upon the use of a first and second sequencing primer. In some embodiments, the first and second sequencing primers are selected to be compatible with a next-generation sequencing method as described herein.

Methods of aligning sequencing reads to known sequence databases of genomic and/or cDNA sequences are well known in the art, and software is commercially available for this process. In some embodiments, reads (less the sequencing primer and/or adapter nucleotide sequence) which do not map, in their entirety, to wild-type sequence databases can be genomic rearrangements or large indel mutations. In some embodiments, reads (less the sequencing primer and/or adapter nucleotide sequence) comprising sequences which map to multiple locations in the genome can be genomic rearrangements. In some embodiments, a de novo assembly of reads overlapping into contiguous sequences, or "contigs," may be built and utilized in the alignment of sequencing reads. In some embodiments, a hot spot reference may be utilized that does not rely on a publicly accessible genomics database.

Samples

In some embodiments, a nucleic acid (e.g., target nucleic acid, nucleic acid comprising a target nucleotide sequence) is present in or obtained from an appropriate sample (e.g., a food sample, environmental sample, biological sample e.g., blood sample, etc.). In some embodiments, the target nucleic acid is a biological sample obtained from a subject. In some embodiments a sample can be a diagnostic sample obtained from a subject. In some embodiments, a sample can further comprise proteins, cells, fluids, biological fluids, preservatives, and/or other substances. By way of non-limiting example, a sample can be a cheek swab, blood, serum, plasma, sputum, cerebrospinal fluid, urine, tears, alveolar isolates, pleural fluid, pericardial fluid, cyst fluid, tumor tissue, tissue, a biopsy, saliva, an aspirate, or combinations thereof. In some embodiments, a sample can be obtained by resection or biopsy.

In some embodiments, the sample can be obtained from a subject in need of treatment for a disease associated with a genetic alteration, e.g., cancer or a hereditary disease. In some embodiments, a known target sequence is present in a disease-associated gene.

In some embodiments, a sample is obtained from a subject in need of treatment for cancer. In some embodiments, the sample comprises a population of tumor cells, e.g., at least one tumor cell. In some embodiments, the sample comprises a tumor biopsy, including but not limited to, untreated biopsy tissue or treated biopsy tissue (e.g., formalin-fixed and/or paraffin-embedded biopsy tissue).

In some embodiments, the sample is freshly collected. In some embodiments, the sample is stored prior to being used in methods and compositions described herein. In some embodiments, the sample is an untreated sample. As used herein, "untreated sample" refers to a biological sample that has not had any prior sample pre-treatment except for dilution and/or suspension in a solution. In some embodiments, a sample is obtained from a subject and preserved or processed prior to being utilized in methods and compositions described herein. By way of non-limiting example, a sample can be embedded in paraffin wax, refrigerated, or frozen. A frozen sample can be thawed before determining the presence of a nucleic acid according to methods and compositions described herein. In some embodiments, the sample can be a processed or treated sample. Exemplary methods for treating or processing a sample include, but are not limited to, centrifugation, filtration, sonication, homogenization, heating, freezing and thawing, contacting with a preservative (e.g., anti-coagulant or nuclease inhibitor) and any combination thereof. In some embodiments, a sample can be treated with a chemical and/or biological reagent. Chemical and/or biological reagents can be employed to protect and/or maintain the stability of the sample or nucleic acid comprised by the sample during processing and/or storage. In addition, or alternatively, chemical and/or biological reagents can be employed to release nucleic acids from other components of the sample. By way of non-limiting example, a blood sample can be treated with an anti-coagulant prior to being utilized in methods and compositions described herein. Suitable methods and processes for processing, preservation, or treatment of samples for nucleic acid analysis may be used in the method disclosed herein. In some embodiments, a sample can be a clarified fluid sample. In some embodiments, a sample can be clarified by low-speed centrifugation (e.g., 3,000×g or less) and collection of the supernatant comprising the clarified fluid sample.

In some embodiments, a nucleic acid present in a sample can be isolated, enriched, or purified prior to being utilized in methods and compositions described herein. Suitable methods of isolating, enriching, or purifying nucleic acids from a sample may be used. For example, kits for isolation of genomic DNA from various sample types are commercially available (e.g., Catalog Nos. 51104, 51304, 56504, and 56404; Qiagen; Germantown, Md.). In some embodiments, methods described herein relate to methods of enriching for target nucleic acids, e.g., prior to a sequencing of the target nucleic acids. In some embodiments, a sequence of one end of the target nucleic acid to be enriched is not known prior to sequencing. In some embodiments, methods described herein relate to methods of enriching specific nucleotide sequences prior to determining the nucleotide sequence using a next-generation sequencing technology. In some embodiments, methods of enriching specific nucleotide sequences do not comprise hybridization enrichment.

Target Genes and Therapeutic Applications

In some embodiments of techniques described herein, a determination of the sequence contiguous to a known oligonucleotide target sequence can provide information relevant to treatment of disease. Thus, in some embodiments, methods disclosed herein can be used to aid in treating disease. In some embodiments, a sample can be from a subject in need of treatment for a disease associated with a genetic alteration. In some embodiments, a known target sequence is a sequence of a disease-associated gene, e.g., an oncogene. In some embodiments, a sequence contiguous to a known oligonucleotide target sequence and/or the known oligonucleotide target sequence can comprise a mutation or genetic abnormality which is disease-associated, e.g., a SNP, an insertion, a deletion, and/or a gene rearrangement. In some embodiments, a sequence contiguous to a known target sequence and/or a known target sequence present in a sample comprised sequence of a gene rearrangement product. In some embodiments, a gene rearrangement can be an oncogene, e.g., a fusion oncogene.

Certain treatments for cancer are particularly effective against tumors comprising certain oncogenes, e.g., a treatment agent which targets the action or expression of a given fusion oncogene can be effective against tumors comprising that fusion oncogene but not against tumors lacking the fusion oncogene. Methods described herein can facilitate a determination of specific sequences that reveal oncogene status (e.g., mutations, SNPs, and/or rearrangements). In some embodiments, methods described herein can further allow the determination of specific sequences when the sequence of a flanking region is known, e.g., methods described herein can determine the presence and identity of gene rearrangements involving known genes (e.g., oncogenes) in which the precise location and/or rearrangement partner are not known before methods described herein are performed.

In some embodiments, a subject is in need of treatment for lung cancer (e.g., with EGFR-TKI, a targeted cancer therapy). In some embodiments, e.g., when the sample is obtained from a subject in need of treatment for lung cancer, the known target sequence can comprise a sequence from a gene selected from the group of ALK, ROS1, and RET. Accordingly, in some embodiments, gene rearrangements result in fusions involving the ALK, ROS1, or RET. Non-limiting examples of gene arrangements involving ALK, ROS1, or RET are described in, e.g., Soda et al. Nature 2007 448561-6: Rikova et al. Cell 2007 131:1190-1203; Kohno et al. Nature Medicine 2012 18:375-7; Takouchi et al. Nature Medicine 2012 18:378-81; which are incorporated by reference herein in their entireties. However, it should be appreciated that the precise location of a gene rearrangement and the identity of the second gene involved in the rearrangement may not be known in advance. Accordingly, in methods described herein, the presence and identity of such rearrangements can be detected without having to know the location of the rearrangement or the identity of the second gene involved in the gene rearrangement.

In some embodiments, the known target sequence can comprise sequence from a gene selected from the group of: ALK, ROS1, and RET.

In some embodiments, the presence of a gene rearrangement of ALK in a sample obtained from a tumor in a subject can indicate that the tumor is susceptible to treatment with a treatment selected from the group consisting of: an ALK inhibitor; EGFR; crizotinib (PF-02341066); AP26113; LDK378; 3-39; AF802; IPI-504; ASP3026; AP-26113; X-396; GSK-1838705A; CH5424802; diamino and aminopyrimidine inhibitors of ALK kinase activity such as NVP-TAE684 and PF-02341066 (see, e.g., Galkin et al., Proc Natl Acad Sci USA, 2007, 104:270-275; Zou et al., Cancer Res, 2007, 67:4408-4417; Hallberg and Palmer F1000 Med Reports 2011 3:21; Sakamoto et al., Cancer Cell 2011 19:679-690; and molecules disclosed in WO 04/079326). All of the foregoing references are incorporated by reference herein in their entireties. An ALK inhibitor can include any agent that reduces the expression and/or kinase activity of ALK or a portion thereof, including, e.g., oligonucleotides, small molecules, and/or peptides that reduce the expression and/or activity of ALK or a portion thereof. As used herein "anaplastic lymphoma kinase" or "ALK" refers to a transmembrane tyROS line kinase typically involved in neuronal regulation in the wildtype form. The nucleotide sequence of the ALK gene and mRNA are known for a number of species, including human (e.g., as annotated under NCBI Gene ID: 238).

In some embodiments, the presence of a gene rearrangement of ROS1 in a sample obtained from a tumor in a subject can indicate that the tumor is susceptible to treatment with a treatment selected from the group consisting of: a ROS1 inhibitor and an ALK inhibitor as described herein above (e.g., crizotinib). A ROS1 inhibitor can include any agent that reduces the expression and/or kinase activity of ROS1 or a portion thereof, including, e.g., oligonucleotides, small molecules, and/or peptides that reduce the expression and/or activity of ROS1 or a portion thereof. As used herein "c-ros oncogene F" or "ROS F" (also referred to in the art as ros-1) refers to a transmembrane tyrosine kinase of the sevenless subfamily and which interacts with PTPN6. Nucleotide sequences of the ROS1 gene and mRNA are known for a number of species, including human (e.g., as annotated under NCBI Gene ID: 6098).

In some embodiments, the presence of a gene rearrangement of RET in a sample obtained from a tumor in a subject can indicate that the tumor is susceptible to treatment with a treatment selected from the group consisting of: a RET inhibitor; DP-2490, DP-3636, SU5416; BAY 43-9006, BAY 73-4506 (regorafenib), ZD6474, NVP-AST487, sorafenib, RPI-1, XL184, vandetanib, sunitinib, imatinib, pazopanib, axitinib, motesanib, gefitinib, and withaferin A (see, e.g., Samadi et al., Surgery 2010 148:1228-36; Cuccuru et al., JNCI 2004 13:1006-1014; Akeno-Stuart et al., Cancer Research 2007 67:6956; Grazma et al., J Clin Oncol 2010 28:15s 5559; Mologni et al., J Mol Endocrinol 2006 37:199-212; Calmomagno et al., Journal NCI 2006 98:326-334; Mologni, Curr Med Chem 2011 18:162-175; and the compounds disclosed in WO 06/034833; US Patent Publication 2011/0201598 and U.S. Pat. No. 8,067,434). All of the foregoing references are incorporated by reference herein in their entireties. A RET inhibitor can include any agent that reduces the expression and/or kinase activity of RET or a portion thereof, including, e.g., oligonucleotides, small molecules, and/or peptides that reduce the expression and/or activity of RET or a portion thereof. As used herein, "rearranged during transfection" or "RET" refers to a receptor tyrosine kinase of the cadherin superfamily which is involved in neural crest development and recognizes glial cell line-derived neurotrophic factor family signaling molecules. Nucleotide sequences of the RET gene and mRNA are known for a number of species, including human (e.g., as annotated under NCBI Gene ID: 5979).

In some embodiments, the known target sequence can comprise a gene selected from Table 2.

TABLE 2

Known target sequences

| GENE | TRANSCRIPT NCBI Reference Sequences (RefSeq) | EXONS | DIRECTION | TYPE |
|---|---|---|---|---|
| AKT3 | NM_005465 | 1, 2, 3 | 5' | Fusion |
| ALK | NM_004304 | 19, (intron19), 20, 21, 22 | 5' | Fusion |
| ARHGAP26 | NM_015071 | 2, 10, 11, 12 | 5' | Fusion |
| AXL | NM_021913 | 19, 20 | 3' | Fusion |
| BRAF | NM_004333 | 7, 8 | 3' | Fusion |
| BRAF | NM_004333 | 7, 8, 9, 10, 11, 12 | 5' | Fusion |
| BRAF | NM_004333 | 15 | 5' | Fusion |
| BRAF | NM_004333 | V600E | n/a | Mutation |
| BRD3 | NM_007371 | 9, 10, 11, 12 | 3' | Fusion |
| BRD4 | NM_014299 | 10, 11 | 3' | Fusion |
| EGFR | NM_005228 | 7, 9, 16, 20 | 5' | Fusion |
| EGFR | NM_005228 | 8 (2-7 exon skipping event) | n/a | Mutation |
| EGFR | NM_005228 | 24, 25 | 3' | Fusion |
| ERG | NM_004449 | 2, 3, 4, 5, 6, 7, 8, 9, 10, 11 | 5' | Fusion |
| ESR1 | NM_001122742 | 3, 4, 5, 6 | 3' | Fusion |
| ETV1 | NM_004956 | 3, 4, 5, 6, 7, 8, 9, 10, 11, 12, 13 | 5' | Fusion |
| ETV4 | NM_001986 | 2, 4, 5, 6, 7, 8, 9, 10 | 5' | Fusion |
| ETV5 | NM_004454 | 2, 3, 7, 8, 9 | 5' | Fusion |
| ETV6 | NM_001987 | 1, 2, 3, 4, 5, 6 | 3' | Fusion |
| ETV6 | NM_001987 | 2, 3, 5, 6, 7 | 5' | Fusion |
| EWSR1 | NM_005243 | 4, 5, 6, 7, 8, 9, 10, 11, 12, 13, 14 | 3' | Fusion |
| FGFR1 | NM_015850 | 2, 8, 9, 10, 17 | 5' | Fusion |
| FGFR2 | NM_000141 | 2, 8, 9, 10 | 5' | Fusion |
| FGFR2 | NM_000141 | 17 | 3' | Fusion |
| FGFR3 | NM_000142 | 17, Intron 17 | 3' | Fusion |
| FGFR3 | NM_000142 | 8, 9, 10 | 5' | Fusion |
| FGR | NM_005248 | 2 | 5' | Fusion |
| INSR | NM_000208 | 20, 21, 22 | 3' | Fusion |
| INSR | NM_000208 | 12, 13, 14, 15, 16, 17, 18, 19 | 5' | Fusion |
| MAML2 | NM_032427 | 2, 3 | 5' | Fusion |
| MAST1 | NM_014975 | 7, 8, 9, 18, 19, 20, 21 | 5' | Fusion |
| MAST2 | NM_015112 | 2, 3, 5, 6 | 5' | Fusion |
| MET | NM_000245 | 13 | 3' | Fusion |
| MET | NM_000245 | 13, 15 (exon 14 skipping event) | n/a | Mutation |
| MSMB | NM_002443 | 2, 3, 4 | 3' | Fusion |
| MUSK | NM_005592 | 7, 8, 9, 11, 12, 13, 14 | 5' | Fusion |
| MYB | NM_001130173 | 7, 8, 9, 11, 12, 13, 14, 15, 16 | 3' | Fusion |
| NOTCH1 | NM_017617 | 2, 4, 29, 30, 31 | 3' | Fusion |
| NOTCH1 | NM_017617 | 26, 27, 28, 29 (internal exon 3-27 deletion) | 5' | Fusion |
| NOTCH2 | NM_024408 | 5, 6, 7 | 3' | Fusion |
| NOTCH2 | NM_024408 | 26, 27, 28 | 5' | Fusion |
| NRG1 | NM_004495 | 1, 2, 3, 6 | 5' | Fusion |
| NTRK1 | NM_002529 | 8, 10, 11, 12, 13 | 5' | Fusion |
| NTRK2 | NM_006180 | 11, 12, 13, 14, 15, 16, 17 | 5' | Fusion |
| NTRK3 | NM_002530 | 13, 14, 15, 16 | 5' | Fusion |
| NTRK3 | NM_001007156 | 15 | 5' | Fusion |
| NUMBL | NM_004756 | 3 | 5' | Fusion |
| NUTM1 | NM_175741 | 3 | 5' | Fusion |
| PDGFRA | NM_006206 | 7 (exon 8 deletion) | n/a | Mutation |
| PDGFRA | NM_006206 | 10, 11, 12, 13, 14, | 5' | Fusion |
| PDGFRA | NM_006206 | T674I, D842V | n/a | Mutation |
| PDGFRB | NM_002609 | 8, 9, 10, 11, 12, 13, 14 | 5' | Fusion |
| PIK3CA | NM_006218 | 2 | 5' | Fusion |
| PKN1 | NM_002741 | 10, 11, 12, 13 | 5' | Fusion |
| PPARG | NM_015869 | 1, 2, 3 | 5' | Fusion |
| PRKCA | NM_002737 | 4, 5, 6 | 5' | Fusion |
| PRKCB | NM_002738 | 3 | 5' | Fusion |
| RAF1 | NM_002880 | 4, 5, 6, 7, 9 | 3' | Fusion |
| RAF1 | NM_002880 | 4, 5, 6, 7, 9, 10, 11, 12 | 5' | Fusion |
| RELA | NM_021975 | 3, 4 | 5' | Fusion |
| RET | NM_020630 | 8, 9, 10, 11, 12, 13 | 5' | Fusion |
| ROS1 | NM_002944 | 31, 32, 33, 34, 35, 36, 37 | 5' | Fusion |
| RSPO2 | NM_178565 | 1,2 | 5' | Fusion |
| RSPO3 | NM_032784 | 2 | 5' | Fusion |
| TERT | NM_198253 | 2 | 5' | Fusion |
| TFE3 | NM_006521 | 2, 3, 4, 5, 6 | 3' | Fusion |

TABLE 2-continued

Known target sequences

| GENE | TRANSCRIPT NCBI Reference Sequences (RefSeq) | EXONS | DIRECTION | TYPE |
|---|---|---|---|---|
| TFE3 | NM_006521 | 2, 3, 4, 5, 6, 7, 8 | 5' | Fusion |
| TFEB | NM_007162 | 1,2 | 5' | Fusion |
| THADA | NM_022065 | 28 | 3' | Fusion |
| TMPRSS2 | NM_005656 | 1, 2, 3, 4, 5, 6 | 3' | Fusion |
| TMPRSS2 | NM_001135099 | 1 | 3' | Fusion |

Further non-limiting examples of applications of methods described herein include detection of hematological malignancy markers and panels thereof (e.g., including those to detect genomic rearrangements in lymphomas and leukemias), detection of sarcoma-related genomic rearrangements and panels thereof; and detection of IGH/TCR gene rearrangements and panels thereof for lymphoma testing.

In some embodiments, methods described herein relate to treating a subject having or diagnosed as having, e.g., cancer with a treatment for cancer. Subjects having cancer can be identified by a physician using current methods of diagnosing cancer. For example, symptoms and/or complications of lung cancer which characterize these conditions and aid in diagnosis are well known in the art and include but are not limited to, weak breathing, swollen lymph nodes above the collarbone, abnormal sounds in the lungs, dullness when the chest is tapped, and chest pain. Tests that may aid in a diagnosis of, e.g., lung cancer include, but are not limited to, x-rays, blood tests for high levels of certain substances (e.g., calcium), CT scans, and tumor biopsy. A family history of lung cancer, or exposure to risk factors for lung cancer (e.g., smoking or exposure to smoke and/or air pollution) can also aid in determining if a subject is likely to have lung cancer or in making a diagnosis of lung cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non-Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chronic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS1tate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors. In some embodiments, the cancer can be lung cancer.

Multiplex Methods

Methods described herein can be employed in a multiplex format. In embodiments of methods described herein, multiplex applications can include determining the nucleotide sequence contiguous to one or more known target nucleotide sequences. As used herein, "multiplex amplification" refers to a process that involves simultaneous amplification of more than one target nucleic acid in one or more reaction vessels. In some embodiments, methods involve subsequent determination of the sequence of the multiplex amplification products using one or more sets of primers. Multiplex can refer to the detection of between about 2-1,000 different target sequences in a single reaction. In some embodiments, however, multiplex can refer to the detection of between about 1,000-10,000 different target sequences in a single reaction. In some embodiments, multiplex can refer to the detection of between about 10,000-100,000 different target sequences in a single reaction. As used herein, multiplex refers to the detection of any range between 2-1,000, e.g., between 5-500, 25-1,000, or 10-100 different target sequences in a single reaction, etc. The term "multiplex" as applied to PCR implies that there are primers specific for at least two different target sequences in the same PCR reaction.

In some embodiments, target nucleic acids in a sample, or separate portions of a sample, can be amplified with a plurality of primers (e.g., a plurality of first and second target-specific primers). In some embodiments, the plurality of primers (e.g., a plurality of first and second target-specific primers) can be present in a single reaction mixture, e.g., multiple amplification products can be produced in the same reaction mixture. In some embodiments, the plurality of primers (e.g., a plurality of sets of first and second target-specific primers) can specifically anneal to known target sequences comprised by separate genes. In some embodiments, at least two sets of primers (e.g., at least two sets of first and second target-specific primers) can specifically anneal to different portions of a known target sequence. In some embodiments, at least two sets of primers (e.g., at least two sets of first and second target-specific primers) can specifically anneal to different portions of a known target sequence comprised by a single gene. In some embodiments, at least two sets of primers (e.g., at least two sets of first and second target-specific primers) can specifically anneal to different exons of a gene comprising a known target sequence. In some embodiments, the plurality of primers (e.g., first target-specific primers) can comprise identical 5' tag sequence portions.

In embodiments of methods described herein, multiplex applications can include determining the nucleotide sequence contiguous to one or more known target nucleotide sequences in multiple samples in one sequencing reaction or sequencing run. In some embodiments, multiple samples can be of different origins, e.g., from different tissues and/or different subjects. In such embodiments, primers (e.g., tailed random primers) can further comprise a barcode portion. In some embodiments, a primer (e.g., a tailed random primer) with a unique barcode portion can be added to each sample and ligated to the nucleic acids therein; the samples can subsequently be pooled. In such embodiments, each resulting sequencing read of an amplification product will comprise a barcode that identifies the sample containing the template nucleic acid from which the amplification product is derived.

EXAMPLES

The following examples are intended to illustrate certain embodiments described herein, including certain aspects of the present invention, but do not exemplify the full scope of the invention.

Example 1: Design of Technology Specific Adapter Nucleic Acids

Adapter nucleic acids and corresponding adapter primers suitable for use in various next-generation sequencing technologies were designed and generated.

An example of an adapter nucleic acid and adapter primers that can be used in Illumina specific applications is shown below:
Illumina Specific Adapter Nucleic Acid and Adapter Primers
Top (Amplification) Strand (5'→3'):
AATGATACGGCGACCACCGAGATCTACACATCCG-TACACACTCTTTCCCTACACG ACGCTCTTC-CGATCTNNNNNNNNNAACCGCCAG-GAG*T (SEQ ID NO.: 1), where "N" represents a nucleotide of a molecular barcode sequence, and "*T" represents a T having a phosphothioate bond.
Bottom (Blocking) Strand (5'→3'):
5phosCTCCTGGCGGTTt (SEQ ID NO.: 2), where "t" represents a modified thymine nucleobase (e.g., an inverted thymine)

```
First adapter primer (5'→3'):
                                 (SEQ ID NO.: 3)
AATGATACGGCGACCACCGAGATCTA Second adapter primer (5'→3'):
                                 (SEQ ID NO.: 4)
ATGATACGGCGACCACCGAGATCTACAC
```

As shown, the first and second adapter primers contain sequences that are identical to a portion of the top (amplification) strand. As a result of this design, each primer is able to prime off of complementary strands generated by a first and second target-specific primer during a first and second PCR step, respectively. The second adapter primer in this example contains two additional nucleotides and is nested relative to the first adapter primer.

An example of an adapter nucleic acid and adapter primers that can be used in Ion semiconductor specific applications is shown below:
Ion Specific Adapter Nucleic Acid and Adapter Primers
Top (Amplification) Strand (5'→3'):
CCATCTCATCCCTGCGTGTCTCCGACTCA-GCTAAGGTAACNNNNNNNNGCTCTTC CGATC*T (SEQ ID NO.: 5), where "N" represents a nucleotide of a molecular barcode sequence, and "*T" represents a T having a phosphothioate bond.
Bottom (Blocking) Strand (5'→3'):
5phosGATCGGAAGAGCt (SEQ ID NO.: 6), where "t" represents a modified thymine nucleobase (e.g., an inverted thymine)

```
First adapter primer (5'→3'):
                                 (SEQ ID NO.: 7)
CCATCTCATCCCTGCGTGTC Second adapter primer (5'→3'):
                                 (SEQ ID NO.: 8)
CCATCTCATCCCTGCGTGTCTCCGACTCAG
```

As shown, the first and second adapter primers contain sequences that are identical to a portion of the top (amplification) strand. As a result of this design, each primer is able to prime off of complementary strands generated by a first and second target-specific primer during a first and second PCR step, respectively. The second adapter primer in this example contains ten additional nucleotides and is nested relative to the first adapter primer.

Example 2: Preparing a Nucleic Acid Sample for Analysis

Figure 5:
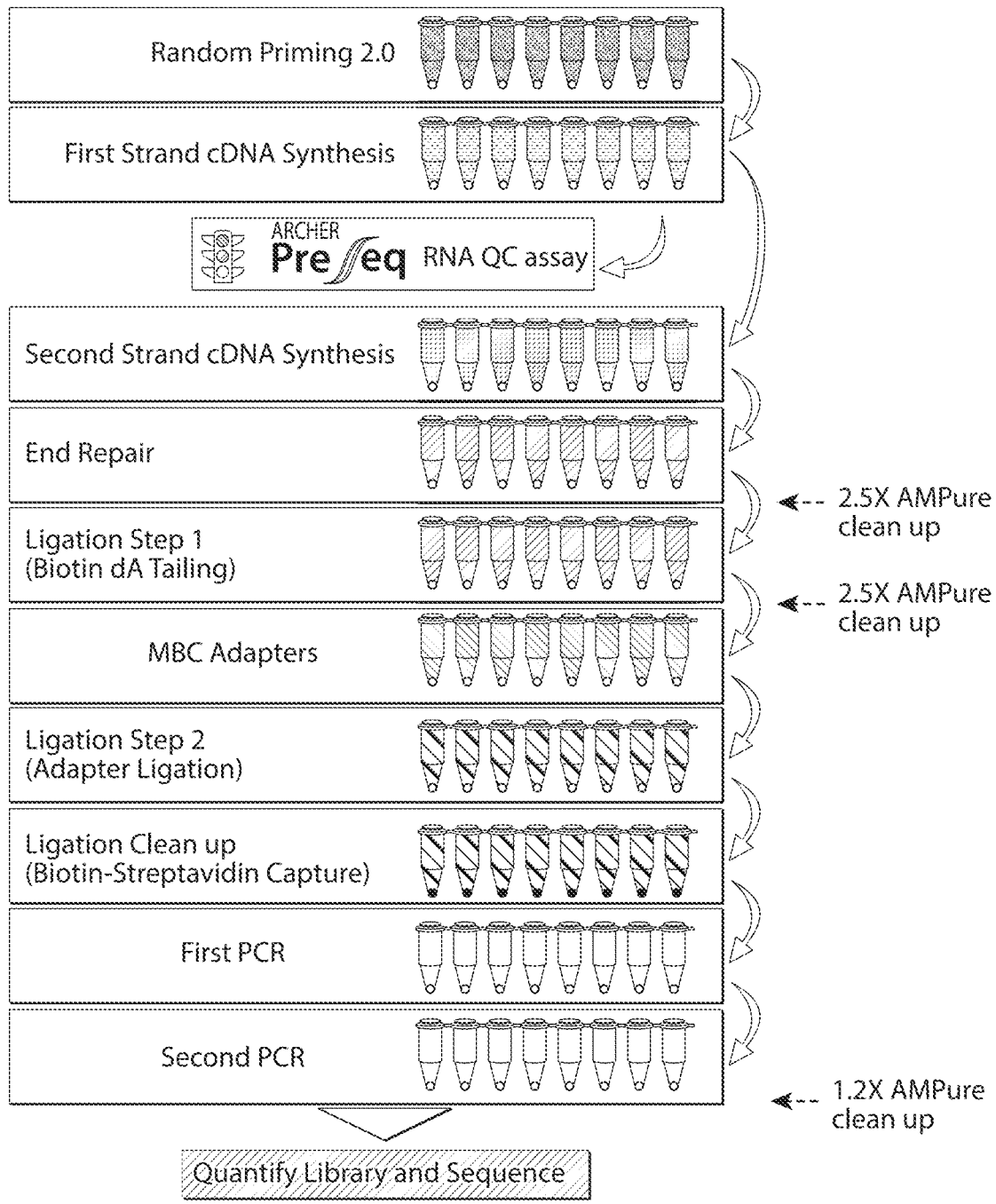
FIG. 5 is a depiction of a workflow for a method of preparing a high-fidelity nucleic acid sample for analysis.

An example of a workflow that illustrates a method of preparing a nucleic acid sample for analysis is shown in FIG. 5. A sample of RNA molecules is annealed with random primers. This annealing can be achieved, for example, by the addition of random hexamers to the sample, followed by heating at 65° C. for 5 minutes. Following annealing, first strand cDNA synthesis is achieved by primer extension (e.g., at room temperature) using a reverse transcriptase enzyme to generate a DNA/RNA hybrid.

At this point, a "PreSeq" RNA QC assay may be performed to assess library complexity. Using this assay, 600 ng of random hexamers (annealed at 65° C. for 5 minutes) was compared to the use of 100 ng of random hexamers (annealed at 65° C. for 5 minutes). The determination of a "Ct" value provides an indication of library complexity and a prediction of the likelihood of molecular barcode inflation during later steps. Generally, a threshold Ct of 28 is used as a benchmark, with values below this threshold being most desirable. It was found that increasing random primer concentration advantageously minimizes Ct.

Following the optional PreSeq assay, RNA of the DNA/RNA hybrid is cleaved, for example, by treating the sample with RnaseH. The resulting fragments of RNA that remain hybridized to the DNA serve as primers for second strand cDNA synthesis. This is achieved using DNA PolI and incubating the sample, e.g., at 16° C. for 60 minutes. Following this period, DNA PolI is inactivated by heat (e.g., by incubating the sample at 75° C. for 20 minutes). It was found that heat inactivation of DNA PolI greatly increased the sample integrity in subsequent sample preparation steps.

Figure 6:
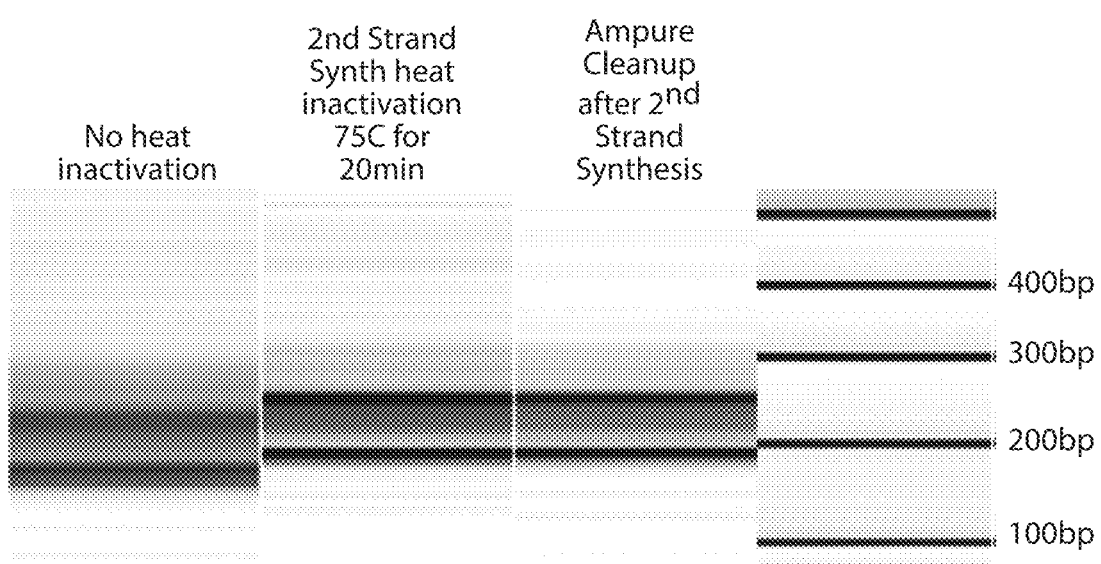
FIG. 6 is an image representation of a gel that depicts a library sample that has been end repaired without polymerase inactivation and a library sample that has been end repaired following heat inactivation of polymerase.

As shown in FIG. 6, heat inactivation of DNA PolI produced samples showing much cleaner bands by gel chromatography following second strand synthesis when compared to no heat inactivation. It is postulated that DNA PolI becomes active during end repair and is damaging fragments due to its 5'→3' and/or 3'→5' exonuclease activity—heat inactivation of DNA PolI following second strand synthesis prevents this from occurring.

The double-stranded cDNA sample is subjected to end repair to blunt end the cDNA and phosphorylate 5' ends. In this step, an excess of T4 DNA Polymerase and T4 Polynucleotide Kinase is added to the sample along with sufficient dNTPs and allowed to incubate (e.g., for 30 minutes at 25° C.). An AMPure cleanup (2.5×) following this period is critical, as it removes residual dATP from the library preparation before tailing with biotin-labeled dATP. This cleanup step prevents the labeling of library fragments with dATP instead of biotin-dATP, which would result in loss of the mislabeled fragments during the capture step.

The library fragments are A-tailed at 3'ends with biotin-labeled dATP in a first ligation step using Klenow Fragment (3'-5' exo-). This can be achieved, for example, by incubating the sample and the necessary components at 37° C. for 15 minutes. An AMPure cleanup (2.5×) following A-tailing is critical, as it removes residual biotin-labeled dATP from the library preparation before the capturing step. This cleanup prevents free biotin-dATP from saturating streptavidin binding sites, resulting in loss of library fragments during capture.

Figure 7:
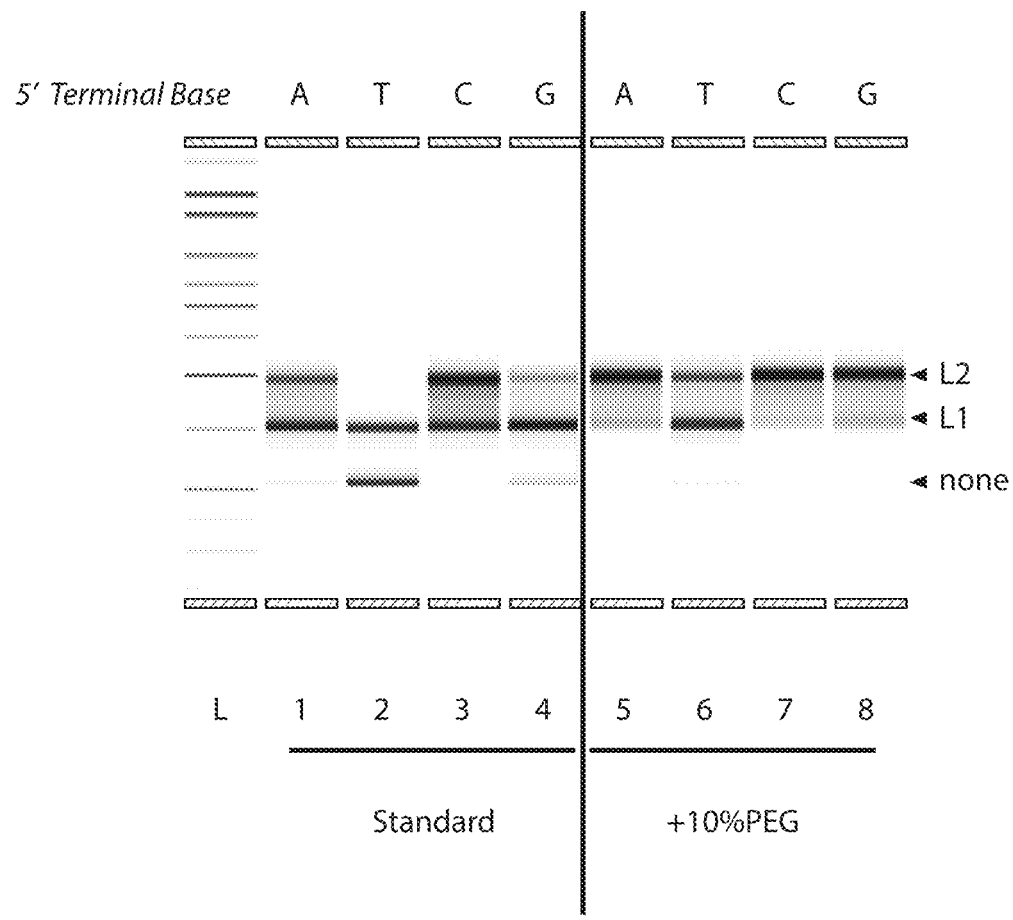
FIG. 7 is an image representation of a gel that depicts adapter ligation efficiencies of samples ligated in the absence or presence of a crowding agent.

In a second ligation step, adapter nucleic acids are ligated to the biotin-A-tailed library fragments using DNA ligase. Interestingly, it was found that the addition of a crowding agent to the ligation mixture greatly improved ligation efficiency across all terminal bases. As shown in FIG. 7, regardless of 5' terminal base, the inclusion of 10% PEG further minimized non-ligated fragments (none) and singly-ligated fragments (L1) while concomitantly increasing doubly-ligated fragments (L2). Moreover, adapter ligation with 10% PEG was achieved in 5 minutes compared to the "Standard" protocol that was performed in 60 minutes. Further data has shown that 20% PEG improves ligation efficiency even further (not shown).

Figure 8A:
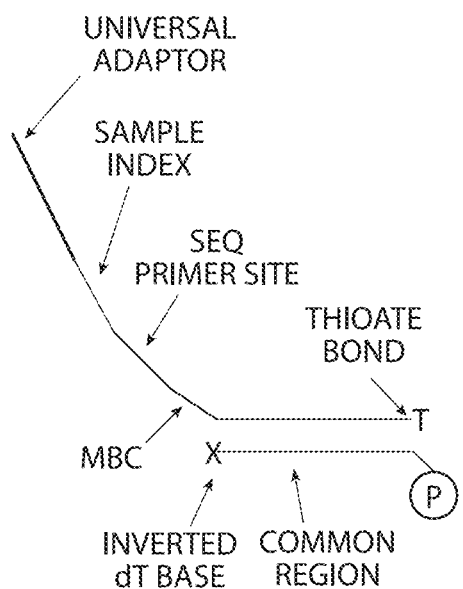
FIG. 8A is a diagram illustrating the components that may comprise an adapter nucleic acid.

FIG. 8A depicts a nucleic acid adapter used in these experiments. As shown, the top strand (amplification strand) contains, in 5'→3', a universal adapter primer site region, a sample index region, a sequencing primer site region, a molecular barcode region, a 3' duplex portion, and a 3' T overhang. The bottom strand (blocking strand) contains a common region that is duplexed with the 3' duplex portion of the top strand, a 5' phosphorylated end, and an inverted dT base that prevents extension of the strand.

Following adapter ligation, ligation cleanup is conducted by capture of library fragments via streptavidin-coated beads. This is performed using M-280 streptavidin dynabeads (10 mg/mL concentration stored in PBS+0.1% BSA+ 0.02% Azide). The storage buffer is exchanged with ligation cleanup buffer (1 M NaCl, 1 mM EDTA, 0.1% Tween, 10 mM Tris pH 8) prior to adding the beads to the sample. The ligated DNA product (50 μL) is mixed with ligation cleanup beads (50 μL for a total of 100 μL). A magnetic field is subsequently applied to the sample to capture library fragments, and the supernatant is removed. Library-bound beads are then transferred to a separate mixture of components for a first PCR step.

A first round of PCR is performed using a first target-specific primer and a first adapter primer. The first adapter primer is identical to at least a portion of the amplification strand, such that it anneals to the complementary strand generated by the first target-specific primer. A second round of PCR is conducted using a second target-specific primer and a second adapter primer, the latter of which is similarly identical to a portion of the amplification strand. The second target-specific primer is nested relative to the first target-specific primer and is further contacted by an additional primer.

Figure 8B:
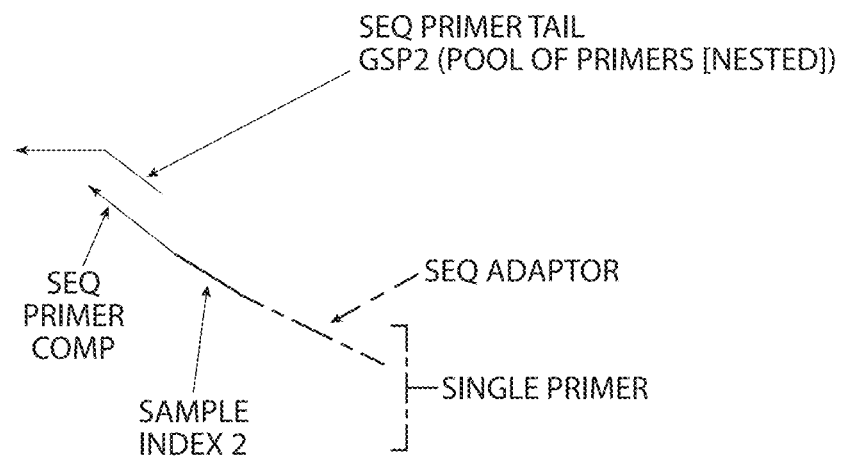
FIG. 8B is a diagram illustrating the components that may comprise a second target-specific primer.

As shown in FIG. 8B, the second target-specific primer contains a 5' tail that does not hybridize to the target-specific region. An additional primer is included that contains a region that is identical to the 5' tail along with a second sample index region and a sequencing adapter region. In this way, the second target-specific primer primes off of the template strand to generate a complement strand having an uncommon tailed region. As in the first round of PCR, the second adapter primes off of this complementary strand to generate a copy of the template strand. As this copy of the template strand will contain a region that is complementary to the 5' tail sequence, the additional primer containing the second sample index region and sequencing adapter region will prime off of this sequence to generate a bottom strand that is ready for sequencing.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of preparing nucleic acids for analysis, the method comprising:
    (a) adding one or more nucleotides to a 3' end of a double-stranded nucleic acid comprising a target nucleotide sequence, wherein at least one of the one or more nucleotides is a capture moiety modified nucleotide;
    (b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double-stranded nucleic acid in step (a);
    (c) capturing the ligation product by contacting the ligation product with a binding partner of the capture moiety modified nucleotide; and
    (d) amplifying the ligation product by polymerase chain reaction using a first target-specific primer that specifically anneals to the target nucleotide sequence and a first adapter primer that specifically anneals to a complementary sequence of the adapter nucleic acid.

2. The method of claim 1, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises the sequence of one or more nucleotides at the 3' end of the adapter nucleic acid that is complementary with the one or more nucleotides added to the 3' end of the double stranded nucleic acid in step (a).

3. The method of claim 1, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

4. The method of claim 1 further comprising:
    (e) amplifying an amplification product of step (d) by polymerase chain reaction using a second adapter primer and a second target-specific primer.

5. The method of claim 4, wherein the second target-specific primer is nested relative to the first target-specific primer.

6. The method of claim 4, wherein the second target-specific primer comprises a 5' tail that does not anneal to the target nucleotide sequence.

7. The method of claim 6, further comprising adding an additional primer comprising a 3' portion that is identical to the 5' tail of the second target-specific primer.

8. The method of claim 1, wherein the capture moiety is a biotin moiety, optionally wherein the biotin moiety is covalently linked to the nucleotide via a linker of 5 to 20 atoms in length.

9. The method of claim 1, wherein the capture moiety modified nucleotide comprises a nucleobase selected from the group consisting of adenine, guanine, thymine, uracil, and cytosine, or derivative(s) thereof.

10. The method of claim 9, wherein the capture moiety modified nucleotide comprises an adenine nucleobase or derivative thereof, optionally wherein the capture moiety is covalently linked to the adenine nucleobase or derivative thereof at position 5, 6, 7 or 8, optionally wherein position 7 of the adenine nucleobase is a carbon atom.

11. The method of claim 1, wherein the binding partner is streptavidin, optionally wherein the streptavidin is attached to a paramagnetic bead.

12. The method of claim 1, wherein, in step (a), one nucleotide is added to the 3' end of the double-stranded nucleic acid comprising the target nucleotide sequence.

13. The method of claim 1 further comprising a washing step after step (a) and before step (b).

14. The method of claim 1 further comprising, prior to step (a), 5' phosphorylating the double-stranded nucleic acid.

15. The method of claim 1 further comprising, prior to step (a):
    i) preparing cDNA by conducting a randomly-primed first strand synthesis reaction using an RNA preparation as a template and a second strand synthesis reaction using a product of the randomly-primed first strand synthesis reaction as a template; and
    ii) end repairing the cDNA to produce a blunt-ended, double-stranded nucleic acid.

16. The method of claim 1, wherein, in step (b), the double-stranded nucleic acid is ligated to the adapter nucleic acid in the presence of a crowding agent, optionally wherein the crowding agent is polyethylene glycol in an amount representing 5% to 50% of the ligation mixture.

17. The method of claim 1, wherein the double-stranded nucleic acid is blunt-ended.

18. A method of preparing nucleic acids for analysis, the method comprising:
    (a) preparing a cDNA by conducting a randomly-primed first strand synthesis reaction using a nucleic acid preparation comprising an RNA as a template and a second strand synthesis reaction using a product of the randomly-primed first strand synthesis reaction as a template, wherein the RNA comprises a target nucleotide sequence;
    (b) end repairing the cDNA to produce a blunt-ended, double-stranded nucleic acid comprising the target nucleotide sequence;
    (c) washing the blunt-ended, double-stranded nucleic acid;
    (d) adding one or more nucleotides to the 3' end of the nucleic acid washed in step (c), wherein at least one of the one or more nucleotides is a capture moiety modified nucleotide;
    (e) washing the nucleic acid produced in step (d);
    (f) ligating an adapter nucleic acid that comprises a ligatable duplex portion and an overhang sequence to the nucleic acid washed in step (e) to produce a ligation product, wherein the overhang sequence is complementary with the one or more nucleotides added in step (d);
    (g) amplifying the ligation product by polymerase chain reaction using a first target-specific primer that specifically anneals to the target nucleotide sequence and a first adapter primer that specifically anneals to a complementary sequence of the adapter nucleic acid;
    (h) amplifying an amplification product of step (g) by polymerase chain reaction using a second adapter primer and a second target-specific primer, wherein the second target-specific primer is nested relative to the first target-specific primer; and
    (i) washing the amplification product of step (h).

19. The method of claim 18, wherein the method further comprises, following step (f) and before step (g), capturing the ligation product using an immobilized binding partner of the capture moiety modified nucleotide.

20. The method of claim 19, further comprising purifying the captured ligation product.

21. The method of claim 19, wherein the binding partner is streptavidin, optionally wherein the streptavidin is attached to a paramagnetic bead.

22. The method of claim 18, wherein the capture moiety modified nucleotide comprises a nucleobase selected from the group consisting of adenine, guanine, thymine, uracil, and cytosine, or a derivative thereof.

23. The method of claim 22, wherein the capture moiety modified nucleotide comprises an adenine nucleobase or derivative thereof, optionally wherein the capture moiety is covalently linked to the adenine nucleobase or derivative thereof at position 5, 6, 7 or 8, optionally wherein position 7 of the adenine nucleobase is a carbon atom.

24. The method of claim 18, wherein the capture moiety is a biotin moiety.

25. The method of claim 24, wherein the biotin moiety is covalently linked to the nucleotide via a linker of 5 to 20 atoms in length.

26. The method of claim 18, wherein the washing steps are performed using a solid-phase reversible immobilization technique.

27. The method of claim 18, wherein the second adapter primer is nested relative to the first adapter primer.

\* \* \* \* \*

SEQUENCE LISTING

```
<160> NUMBER OF SEQ ID NOS: 8

<210> SEQ ID NO 1
<211> LENGTH: 91
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (71)..(78)
<223> OTHER INFORMATION: n is a, c, g, or t

<400> SEQUENCE: 1
aatgatacgg cgaccaccga gatctacaca tccgtacaca ctctttccct acacgacgct    60
cttccgatct nnnnnnnnaa ccgccaggag t                                   91

<210> SEQ ID NO 2
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 2
ctcctggcgg ttt                                                       13

<210> SEQ ID NO 3
```

```
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 3
aatgatacgg cgaccaccga gatcta                                          26

<210> SEQ ID NO 4
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 4
atgatacggc gaccaccgag atctacac                                        28

<210> SEQ ID NO 5
<211> LENGTH: 61
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (41)..(48)
<223> OTHER INFORMATION: n is a, c, g, or t

<400> SEQUENCE: 5
ccatctcatc cctgcgtgtc tccgactcag ctaaggtaac nnnnnnnngc tcttccgatc     60
t                                                                     61

<210> SEQ ID NO 6
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 6
gatcggaaga gct                                                        13

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ccatctcatc cctgcgtgtc                                                 20

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
ccatctcatc cctgcgtgtc tccgactcag                                      30
```